United States Patent
Shiota et al.

(10) Patent No.: US 9,902,675 B2
(45) Date of Patent: *Feb. 27, 2018

(54) VINYL-GROUP-CONTAINING FLUORENE COMPOUND

(71) Applicants: TOKYO OHKA KOGYO CO., LTD., Kawasaki-shi (JP); DAICEL CORPORATION, Osaka-shi (JP)

(72) Inventors: Dai Shiota, Kawasaki (JP); Kunihiro Noda, Kawasaki (JP); Hiroki Chisaka, Kawasaki (JP); Yasuyuki Akai, Himeji (JP); Ichiro Takase, Himeji (JP); Yoshiya Narasaki, Himeji (JP); Daisuke Tanida, Himeji (JP); Kyuhei Kitao, Himeji (JP)

(73) Assignees: TOKYO OHKA KOGYO CO., LTD., Kawasaki-Shi (JP); DAICEL CORPORATION, Osaka-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/780,760

(22) PCT Filed: Mar. 28, 2014

(86) PCT No.: PCT/JP2014/059311
§ 371 (c)(1),
(2) Date: Sep. 28, 2015

(87) PCT Pub. No.: WO2014/157676
PCT Pub. Date: Oct. 2, 2014

(65) Prior Publication Data
US 2016/0046551 A1 Feb. 18, 2016

(30) Foreign Application Priority Data
Mar. 29, 2013 (JP) .................. 2013-075395

(51) Int. Cl.
C07C 57/50 (2006.01)
C07C 69/54 (2006.01)
(Continued)

(52) U.S. Cl.
CPC ............ C07C 43/215 (2013.01); C07C 41/22 (2013.01); C07C 41/24 (2013.01); C07C 43/225 (2013.01);
(Continued)

(58) Field of Classification Search
CPC ..... C07C 2603/18; C07C 57/50; C07C 69/54; G03F 7/027
See application file for complete search history.

(56) References Cited

U.S. PATENT DOCUMENTS 4,069,056 A 1/1978 Crivello
4,473,626 A 9/1984 Molaire et al.
(Continued)

FOREIGN PATENT DOCUMENTS

CN 101685165 A 3/2010
EP 0428706 A1 5/1991
(Continued)

OTHER PUBLICATIONS

Shoji Kajigaeshi (Journal of the Chemical Society of Japan., 1989, (10), p. 1757-1764).*
(Continued)

*Primary Examiner* — Valerie Rodriguez-Garcia
(74) *Attorney, Agent, or Firm* — Knobbe Martens Olson & Bear LLP

(57) ABSTRACT

A novel vinyl-group-containing fluorene compound and a method for producing the same, a polymerizable monomer and cross-linking agent including this compound, a leaving-group-containing fluorene compound, a monovinyl-group-containing fluorene compound, and methods for producing the same. This vinyl-group-containing fluorene compound is represented by formula (1). In the formula, $W^1$ and $W^2$ represent a group represented by formula (2), a group represented by formula (4), a hydroxyl group, or a (meth)acryloyloxy group, $R^{3a}$ and $R^{3b}$ represent a cyano group, a halogen atom, or a monovalent hydrocarbon, and n1 and n2 are integers of 0-4. In formulas (2) and (4), a ring (Z) is an aromatic hydrocarbon ring, X is a single bond or a group represented by —S—, $R^1$ is a single bond or a C1-4 alkylene group, $R^2$ is a specific substituent group such as a monovalent hydrocarbon, and m is an integer of 0 or greater.

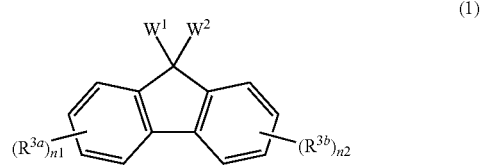

(1)

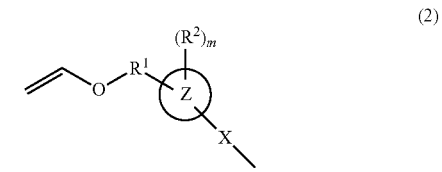

(2)

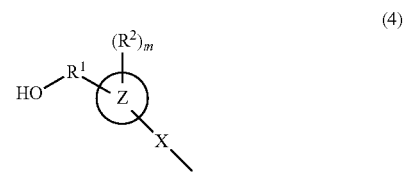

(4)

2 Claims, No Drawings

(51) Int. Cl.
| | |
|---|---|
| G03F 7/027 | (2006.01) |
| C07C 43/215 | (2006.01) |
| C07C 43/23 | (2006.01) |
| C07C 309/66 | (2006.01) |
| C07C 41/22 | (2006.01) |
| C07C 41/24 | (2006.01) |
| C07C 43/225 | (2006.01) |
| C07C 67/14 | (2006.01) |
| C07C 303/30 | (2006.01) |

(52) U.S. Cl.
CPC .............. *C07C 43/23* (2013.01); *C07C 57/50* (2013.01); *C07C 67/14* (2013.01); *C07C 69/54* (2013.01); *C07C 303/30* (2013.01); *C07C 309/66* (2013.01); *G03F 7/027* (2013.01); *C07C 2603/18* (2017.05)

(56) References Cited

U.S. PATENT DOCUMENTS

| | | | |
|---|---|---|---|
| 5,176,977 A * | 1/1993 | Molaire | C07C 69/017 430/109.4 |
| 7,534,547 B2 | 5/2009 | Hanabata et al. | |
| 2003/0064168 A1 | 4/2003 | Kato et al. | |
| 2003/0211421 A1 | 11/2003 | Hanabata et al. | |
| 2004/0106004 A1* | 6/2004 | Li | C07C 211/61 428/690 |
| 2005/0158659 A1* | 7/2005 | Lee | G03F 7/0007 430/271.1 |
| 2005/0175930 A1 | 8/2005 | Lee | |
| 2006/0166114 A1 | 7/2006 | Lee | |
| 2007/0117876 A1 | 5/2007 | Lee | |
| 2008/0220372 A1 | 9/2008 | Lee et al. | |
| 2009/0068569 A1* | 3/2009 | Seta | G03F 7/027 430/2 |
| 2010/0076138 A1 | 3/2010 | Iwasa | |
| 2016/0046551 A1 | 2/2016 | Shiota et al. | |
| 2016/0046552 A1 | 2/2016 | Shiota et al. | |
| 2016/0046742 A1 | 2/2016 | Shiota et al. | |

FOREIGN PATENT DOCUMENTS

| | | |
|---|---|---|
| EP | 0598552 A2 | 5/1994 |
| EP | 2980057 A1 | 3/2014 |
| EP | 2980058 A1 | 3/2014 |
| EP | 2980059 A1 | 2/2016 |
| JP | 2000-178115 A | 6/2000 |
| JP | 2002-255929 A | 9/2002 |
| JP | 2004-137262 | 5/2004 |
| JP | 2006-152115 | 6/2006 |
| JP | 2006-282875 A | 10/2006 |
| JP | 2006-327990 A | 12/2006 |
| JP | 2009-013096 | 1/2009 |
| JP | 2009-215447 A | 9/2009 |
| JP | 2010-037470 A | 2/2010 |
| JP | 2010-097194 | 4/2010 |
| JP | 2011-090774 | 5/2011 |
| JP | 2011-201791 | 10/2011 |
| JP | 2012-063728 A | 3/2012 |
| JP | 2012-068652 A | 4/2012 |
| JP | 2012-118551 A | 6/2012 |
| JP | 2013-028574 * | 2/2013 |
| JP | 2013-028574 A | 2/2013 |
| KR | 10-2003-0005419 A | 1/2003 |
| WO | WO 90/15043 A2 | 12/1990 |
| WO | WO2002/079131 | 10/2002 |
| WO | WO2006/132139 | 12/2006 |
| WO | WO2013/018302 | 2/2013 |
| WO | WO2013/022065 A1 | 3/2015 |

OTHER PUBLICATIONS

CAS reaction database (Jun. 28, 2001)—included in the office action.*

Carrie Y. K. Chan et al: "Polycyclotrimerization of Dinitriles: A New Polymerization Route for the Construction of Soluble Nitrogen-Rich Polytriazines with Hyperbranched Structures and Functional Properties", Macromolecules, vol. 46, No. 24, Dec. 23, 2013, pp. 9494-9506, XP055251844, US.

Ching-Nan Chuang et al: "Synthesis and characterization of fluorene-derived PU as a thermo cross-linked hole-transporting layer for PLED", Polymer., vol. 53, No. 10, Apr. 1, 2012, pp. 2001-2007, XP055250560 GB.

Database CAPLUS [Online] Chemical Abstracts Service, Columbus, Ohio, US ; XP002754507 , retrieved from STN accession No. 80826-88-6P Database accession No. 1978:423387 * abstract * & Lewis, Terry Warren TI—Dehydration Reactions in the Organic Solid State : "Dehydration reactions in the organic solid state", INT, 1977.

Gyoo-Soon Park et al: "H-Bonding Controls the Regio-selectivities on the Acid-catalyzed Reaction of fluorenone with Phenol Derivatives", Bulletin of the Korean Chemical Society, vol . 31, No. 7, Jul. 20, 2010 , pp. 1837-1838, XP055251273, KR.

Mitsuaki Yamada et al: "Synthesi s of Fl uorenebi sphenoxy Deri vatives by Acid-sulfur Compound Catalyzed Condensation Reaction", Chemistry Letters, Chemical Society of Japan, Japan, vol. 10, Jan. 1, 1998, pp. 1055-1056, XP002361848.

Shoji Kajigaeshi et al: "Spirofluorenes.V. Synthesis of spirofluorenes containing o-phenylene group in their system.", Nippon Kagaku Kaishi : Journal of the Chemical Society of Japan., No. 10, Jan. 1, 1989, pp. 1757-1764, XP055251263, JP.

Toshihide Hasegawa et al: "Diphenolic9,9-Diarylfluorene Trimers and Derivatives Possessing Flexible Al kylene Chain Spacers: Synthesi s of the Monomers, Their Polymerization, and Properties of the Resulting Polymers", Macromolecules, vol. 43, No. 1, Jan. 12, 2010, pp. 131-136, XP055251841, US.

Yoshihisa Okamoto et al: "Novel vinyl ether thermosetting resins", Polymer, Jan. 1, 1993, pp. 691-695, XP055251276, DOI: 10.1016/0032-3861(93)90349-F.

Partial supplementary European search report in European Patent Application No. 14775291.9 dated Mar. 24, 2016.

Sadaaki Nunomoto et al: "Properties of polymers cross-linked by a fluorene ring or siloxane-containing cross-linking agents", Designed Monomers and Polymers, vol. 4, No. 1, Mar. 1, 2001, pp. 1-8, XP055286865, NL ISSN: 1385-772X.

Extended European search report in European Patent Application No. 14775291.9, dated Jul. 25, 2016.

Konrad H. Bleicher, et al., New phenylfluorenyl based linkers for solid phase synthesis, Tetrahedron Letters, 2000, 41(47), pp. 9037-9042, Scheme 1. Compound(4).

Marilia O. F. Goulart, et al., Electroorganic Reactions. 31. Quinonemethide Radical-Anions and Dianions: Their Cathodic Generation and Reactivity, Journal of Organic Chemistry, 1988, 53(11), pp. 2520-2525, p. 2521 Compound (23).

Bohumir Koutek et al., Perturbation of the Fuchsone Chromophore by 3, 5-Methyl Substitusion. Sterically Crowded Exocyclic Double Bond, Collection of Czechoslovak Chemical Communications, 1981, 46(10), pp. 2540-2556, p. 2547 Scheme 3.

Hans-Dieter Becker, et al., Preparation and Reactions of 2, 6-Ditert-butyl-4-(9-fluorenylidene)-1, 4-benzoquinone, Journal of Organic Chemistry, 1976, 41(2), pp. 214-221, Table II Compound 11a.

Martin Stiles, et al., Tribenzotropone from a 1, 3-Rearrangement, Journal of Organic Chemistry, 1957, 22, pp. 1243-1246, p. 1245 9-o-hydroxyphenyl-9-fluorenol.

Office Action issued in Korean Patent Application No. 10-2015-7030995, dated May 4, 2017.

Nelson Felix et al., Acid-Labile, Chain-Scission Polymer Systems Used as Positive-Tone Photoresists Developable in Supercritical CO2, Chem. Mater., 2008, 20(9), pp. 2932-2936, Abstract, Fig. 2-3, Scheme 1.

Nelson M. Felix et al., Achieving Small Dimensions with an Environmentally Friendly Solvent: Photoresist Development Using Supercritical CO2, Proc. of SPIE, 2008, vol. 6923, pp. 69233L-1-69233L-11, Abstract, Fig. 6.

Extended European search report in European Patent Application No. 14774297.7, dated Mar. 14, 2016.

(56) References Cited

OTHER PUBLICATIONS

International Search Report in International Application No. PCT/JP2014/059308, dated Apr. 22, 2014.
Office Action in Chinese Patent Application No. 201480018794.2, dated Apr. 25, 2016.
Office Action in Korean Patent Application No. 10-2015-7030693, dated Oct. 14, 2016.
Office Action in U.S. Appl. No. 14/780,743, dated Dec. 23, 2016.
Office Action for U.S. Appl. No. 14/780,786 dated, Feb. 2, 2017.
Office Action in U.S. Appl. No. 14/780,786, dated Aug. 11, 2016.
Partial supplementary European search report for European Patent Application No. 14773950.2, dated Mar. 9, 2016.
Office Action issued in Korean Patent Application No. 10-2015-7030693, dated Jun. 20, 2017.
Office Action in U.S. Appl. No. 14/780,786, dated Aug. 3, 2017.
Encyclopedia of Polymer Science and Technology, vol. 10, Mar. 2004, pp. 807-836.
Office Action issued in U.S. Appl. No. 14/780,743, dated Sep. 25, 2017.

\* cited by examiner

VINYL-GROUP-CONTAINING FLUORENE COMPOUND

This application is the U.S. National Phase under 35 U.S.C. §371 of International Application PCT/JP2014/059311, filed Mar. 28, 2014, designating the U.S., and published in Japanese as WO 2014/157676 on Oct. 2, 2014, which claims priority to Japanese Patent Application No. 2013-075395, filed Mar. 29, 2013, the entire contents of which are incorporated herein by reference.

The present invention was made pursuant to a joint research agreement between Tokyo Ohka Kogyo Co., Ltd. and Daicel Corporation.

TECHNICAL FIELD

The present invention relates to a vinyl-group-containing fluorene-based compound, a polymerizable monomer including the vinyl-group-containing fluorene-based compound, a crosslinking agent including the vinyl-group-containing fluorene-based compound, a process for producing the vinyl-group-containing fluorene-based compound, a leaving group-containing fluorene-based compound, a process for producing a monovinyl-group-containing fluorene-based compound, a monovinyl-group-containing fluorene-based compound, a monovinyl group- and mono(meth)acryloyloxy group-containing fluorene-based compound, and a (meth)acryloyloxy group-containing fluorene-based compound, and a process for producing the same.

BACKGROUND ART

Compounds having a fluorene skeleton (for example, 9,9-bisphenylfluorene skeleton) are known to have excellent functions in terms of optical properties such as light transmittance and refractive index and thermal properties such as heat resistance. Therefore, compounds having a fluorene skeleton are used as raw materials for optical members such as lenses, prisms, filters, image display materials, optical disk substrates, optical fibers, optical waveguides, casing materials, films, and coating materials. Such compounds having a fluorene skeleton include, for example, compounds disclosed in Patent Literature 1.

Patent Document 1: Japanese Unexamined Patent Application, Publication No. 2011-201791

DISCLOSURE OF THE INVENTION

Problems to be Solved by the Invention

An object of the present invention is to provide a novel vinyl-group-containing fluorene-based compound, a polymerizable monomer including the vinyl-group-containing fluorene-based compound, a crosslinking agent including the fluorene-based compound, a process for producing the vinyl-group-containing fluorene-based compound, a leaving group-containing fluorene-based compound, a process for producing a monovinyl-group-containing fluorene-based compound, a monovinyl-group-containing fluorene-based compound, a monovinyl group- and mono(meth)acryloyloxy group-containing fluorene-based compound, and a (meth)acryloyloxy group-containing fluorene-based compound, and a process for producing the same.

Means for Solving the Problems

The present inventors have made extensive and intensive studies with a view to solving the above problems. As a result, the present inventors have found novel vinyl-group-containing fluorene-based compounds, leading to the completion of the present invention. Specifically, the present invention provides the following matters.

According to one aspect of the present invention, there is provided a vinyl-group-containing fluorene-based compound represented by the following general formula (1):

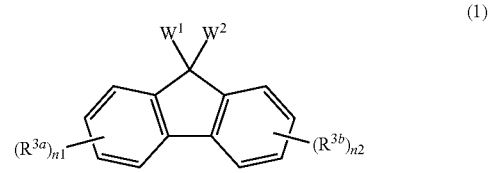

(1)

wherein $W^1$ and $W^2$ each independently represent a group represented by the following general formula (2), a group represented by the following general formula (4), a hydroxyl group, or a (meth)acryloyloxy group, provided that $W^1$ and $W^2$ do not simultaneously represent a hydroxyl group or the group represented by the following general formula (4); $R^{3a}$ and $R^{3b}$ each independently represent a cyano group, a halogen atom, or a monovalent hydrocarbon group; and n1 and n2 each independently represent an integer of 0 to 4,

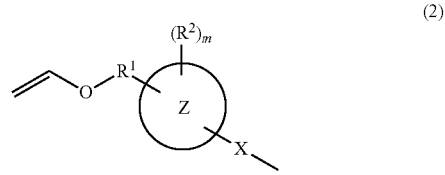

(2)

wherein a ring Z represents an aromatic hydrocarbon ring; X represents a single bond or a group represented by —S—; $R^1$ represents a single bond or an alkylene group having 1 to 4 carbon atoms; $R^2$ represents a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a sulfo group, or a group formed by substituting at least a part of hydrogen atoms bonded to carbon atoms contained in a monovalent hydrocarbon group, a group represented by —$OR^{4a}$, a group represented by —$SR^{4b}$, an acyl group, an alkoxycarbonyl group, a group represented by —$NHR^{4c}$, or a group represented by —$N(R^{4d})_2$ with a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group; $R^{4a}$ to $R^{4d}$ each independently represent a monovalent hydrocarbon group; and m is an integer of 0 or more, and

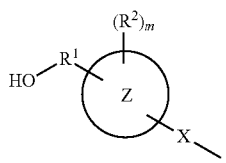

(4)

wherein a ring Z, X, $R^1$, $R^2$, and m are as defined above.

According to a second aspect of the present invention, there is provided a polymerizable monomer comprising the above vinyl-group-containing fluorene-based compound.

According to a third aspect of the present invention, there is provided a crosslinking agent comprising the above vinyl-group-containing fluorene-based compound wherein $W^1$ and $W^2$ each are independently the group represented by the general formula (2) or a (meth)acryloyloxy group.

According to a fourth aspect of the present invention, there is provided a process for producing a vinyl-group-containing fluorene-based compound, the process comprising obtaining a vinyl-group-containing fluorene-based compound represented by the following general formula (1a) from a hydroxyl group-containing fluorene-based compound represented by the following general formula (3) through a leaving group-containing fluorene-based compound represented by the following general formula (5):

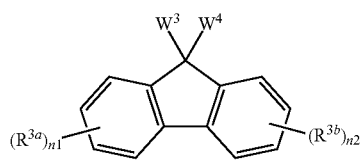

(3)

wherein $W^3$ and $W^4$ each independently represent a group represented by the above general formula (4) or a hydroxyl group, provided that $W^3$ and $W^4$ do not simultaneously represent a hydroxyl group; and $R^{3a}$, $R^{3b}$, n1, and n2 are as defined above,

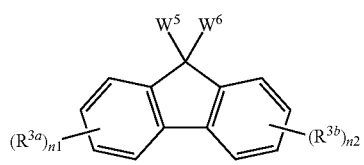

(5)

wherein $W^5$ and $W^6$ each independently represent a group represented by the following general formula (6) or a hydroxyl group, provided that $W^5$ and $W^6$ do not simultaneously represent a hydroxyl group; and $R^{3a}$, $R^{3b}$, n1, and n2 are as defined above,

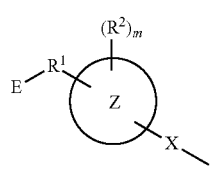

(6)

wherein E represents an alkyloxy group having 1 to 4 carbon atoms and substituted with a chlorine atom, a bromine atom, an iodine atom, a methanesulfonyloxy group, a trifluoromethanesulfonyloxy group, a p-toluenesulfonyloxy group, or a benzenesulfonyloxy group; and a ring Z, X, $R^1$, $R^2$, and m are as defined above,

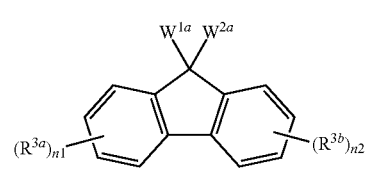

(1a)

wherein $W^{1a}$ and $W^{2a}$ each independently represent a group represented by the above general group (2), a group represented by the general formula (4), a hydroxyl group, or a (meth)acryloyloxy group, provided that $W^{1a}$ and $W^{2a}$ simultaneously represent none of a hydroxyl group, a group represented by the general formula (4), and a (meth)acryloyloxy group; and $R^{3a}$, $R^{3b}$, n1, and n2 are as defined above.

According to a fifth aspect of the present invention, there is provided a leaving group-containing fluorene-based compound represented by the above general formula (5).

According to a sixth aspect of the present invention, there is provided a process for producing a vinyl-group-containing fluorene-based compound, the process comprising obtaining a vinyl-group-containing fluorene-based compound represented by the general formula (1a) from a hydroxyalkyloxy group-containing fluorene-based compound represented by the general formula (7) through a leaving group-containing fluorene-based compound represented by the general formula (5):

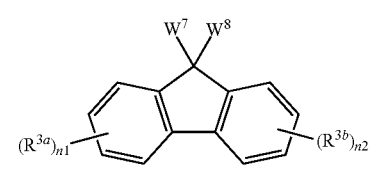

(7)

$W^7$ and $W^8$ each independently represent a group represented by the following general formula (8) or a hydroxyl group, provided that $W^7$ and $W^8$ do not simultaneously represent a hydroxyl group; and $R^{3a}$, $R^{3b}$, n1, and n2 are as defined above,

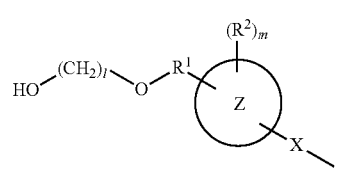

(8)

wherein l represents an integer of 1 to 4; a ring Z, X, $R^1$, $R^2$, and m are as defined above.

According to a seventh aspect of the present invention, there is provided a process for producing a monovinyl-group-containing fluorene-based compound, the process comprising obtaining a monovinyl-group-containing fluorene-based compound represented by the following general formula (9) from a leaving group-containing fluorene-based compound represented by the following general formula (5a).

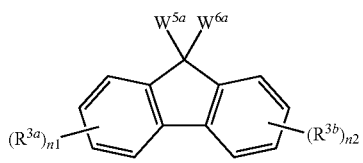

(5a)

wherein $W^{5a}$ and $W^{6a}$ each represent a group represented by the above general formula (6); and $R^{3a}$, $R^{3b}$, n1, and n2 are as defined above,

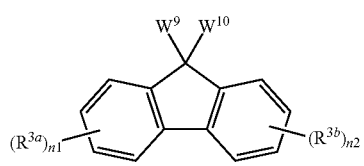

(9)

wherein any one of $W^9$ and $W^{10}$ represents a group represented by the general formula (2) while the other represents a group represented by the general formula (6); and $R^{3a}$, $R^{3b}$, n1, and n2 are as defined above.

According to an eighth aspect of the present invention, there is provided a monovinyl-group-containing fluorene-based compound represented by the general formula (9).

According to a ninth aspect of the present invention, there is provided a monovinyl group- and mono(meth)acryloyloxy group-containing fluorene-based compound represented by the following general formula (10):

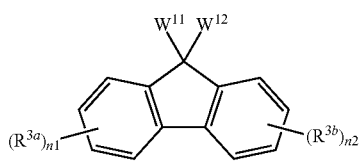

(10)

wherein any one of $W^{11}$ and $W^{12}$ represents a group represented by the above general formula (2) while the other represents a group represented by the following general formula (11) or (12); $R^{3a}$ and $R^{3b}$ each independently represent a cyano group, a halogen atom, or a monovalent hydrocarbon group; and n1 and n2 each independently represent an integer of 0 to 4,

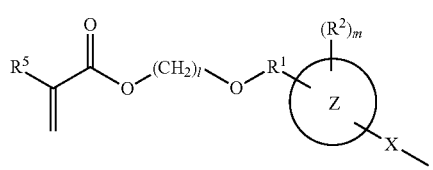

(11)

wherein $R^5$ represents a hydrogen atom or a methyl group; and a ring Z, X, $R^1$, $R^2$, m, and l are as defined above,

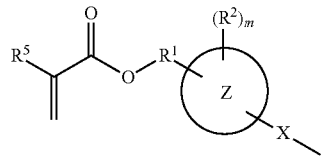

(12)

wherein a ring Z, X, $R^1$, $R^2$, $R^5$, and m are as defined above.

According to a tenth aspect of the present invention, there is provided a (meth)acryloyloxy group-containing fluorene-based compound represented by the following general formula (19):

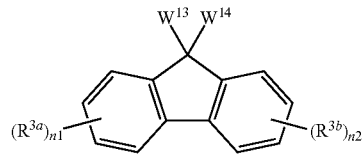

(19)

wherein $W^{13}$ and $W^{14}$ each independently represent a group represented by the above general formula (12), a hydroxyl group, or a (meth)acryloyloxy group, provided that at least one of $W^{13}$ and $W^{14}$ represents a group represented by the above general formula (12); and $R^{3a}$, $R^{3b}$, n1, and n2 are as defined above.

According to an eleventh aspect of the present invention, there is provided a process for producing a (meth)acryloyloxy group-containing fluorene-based compound, the process comprising obtaining a (meth)acryloyloxy group-containing fluorene-based compound represented by the general formula (19) from a hydroxyl group-containing fluorene-based compound represented by the general formula (3).

Effects of the Invention

The present invention can provide a novel vinyl-group-containing fluorene-based compound, a polymerizable monomer including the vinyl-group-containing fluorene-based compound, a crosslinking agent including the fluorene-based compound, a process for producing the vinyl-group-containing fluorene-based compound, a leaving group-containing fluorene-based compound, a process for producing a monovinyl-group-containing fluorene-based compound, a monovinyl-group-containing fluorene-based compound, a monovinyl group- and mono(meth)acryloyloxy group-containing fluorene-based compound, and a (meth)acryloyloxy group-containing fluorene-based compound, and a process for producing the same.

PREFERRED MODE FOR CARRYING OUT THE INVENTION

Vinyl-Group-Containing Fluorene-Based Compound Represented by General Formula (1)

The vinyl-group-containing fluorene-based compound according to the present invention is represented by the following general formula (1):

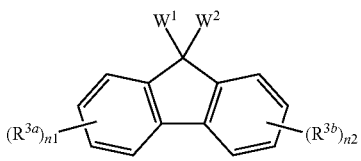

(1)

In the general formula (1), $W^1$ and $W^2$ each independently represent a group represented by the following general formula (2), a group represented by the following general formula (4), a hydroxyl group, or a (meth)acryloyloxy group, provided that $W^1$ and $W^2$ do not simultaneously represent a hydroxyl group or a group represented by the following general formula (4). Preferably, at least one of W1 and W2 represents a group represented by the following general formula (2). More preferably, both $W^1$ and $W^2$ represent a group represented by the following general formula (2). The term "(meth)acryloyl" as used herein means both acryloyl and methacryloyl.

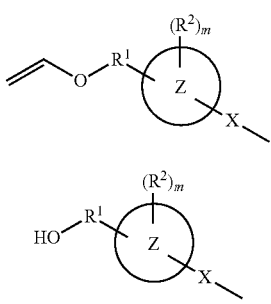

In the general formulae (2) and (4), examples of the ring Z include benzene ring and fused polycyclic aromatic hydrocarbon rings [for example, fused di- to tetracyclic aromatic hydrocarbon rings such as fused dicyclic hydrocarbon rings (for example, $C_{8-20}$ fused dicyclic hydrocarbon rings, preferably $C_{10-16}$ fused dicyclic hydrocarbon rings, such as naphthalene ring) and fused tricyclic aromatic hydrocarbon rings (for example, anthracene ring or phenanthrene ring). The ring Z is preferably a benzene ring or a naphthalene ring, more preferably a naphthalene ring. When both $W^1$ and $W^2$ represent a group represented by the general formula (2), or when one of $W^1$ and $W^2$ represent a group represented by the general formula (2) while the other represents a group represented by the general formula (4), the ring Z contained in $W^1$ may be the same as or different from the ring Z contained in $W^2$. For example, one of the rings may represent a benzene ring with the other ring representing a naphthalene ring or the like. Particularly preferably, both the rings represent a naphthalene ring. The position of substitution of the ring Z bonded through X to the 9-position of fluorene is not particularly limited. For example, when the ring Z represents a naphthalene ring, the group corresponding to the ring Z bonded to the 9-position of fluorene may be, for example, a 1-naphthyl group or a 2-naphthyl group.

In the general formulae (2) and (4), X each independently represent a single bond or a group represented by —S—, typically a single bond.

In the general formulae (2) and (4), examples of $R^1$ include single bond; and alkylene groups having 1 to 4 carbon atoms such as methylene, ethylene, trimethylene, propylene, and butane-1,2-diyl groups. Single bond and $C_{2-4}$ alkylene groups (particularly $C_{2-3}$ alkylene groups such as ethylene and propylene groups) are preferred, and a single bond is more preferred. When both $W^1$ and $W^2$ represent a group represented by the general formula (2), or when one of $W^1$ and $W^2$ represents a group represented by the general formula (2) while the other represents a group represented by the general formula (4), $R^1$ contained in $W^1$ may be the same as or different from $R^1$ contained in $W^2$.

In the general formulae (2) and (4), examples of $R^2$ include monovalent hydrocarbon group such as alkyl groups (for example, $C_{1-12}$ alkyl groups such as methyl, ethyl, propyl, isopropyl, and butyl groups, preferably $C_{1-8}$ alkyl groups, more preferably $C_{1-6}$ alkyl groups), cycloalkyl groups (for example, $C_{5-10}$ cycloalkyl groups such as cyclohexyl group, preferably $C_{5-8}$ cycloalkyl groups, more preferably $C_{5-6}$ cycloalkyl groups), aryl groups (for example, $C_{6-14}$ aryl groups such as phenyl, tolyl, xylyl, and naphthyl groups, preferably $C_{6-10}$ aryl groups, more preferably $C_{6-8}$ aryl groups), and aralkyl groups (for example, $C_{6-10}$ aryl $C_{1-4}$ alkyl groups such as benzyl and phenethyl groups); hydroxyl group; groups represented by —$OR^{4a}$ wherein $R^{4a}$ represents a monovalent hydrocarbon group (for example, the above-exemplified monovalent hydrocarbon group) such as alkoxy groups (for example, $C_{1-12}$ alkoxy groups such as methoxy, ethoxy, propoxy, and butoxy groups, preferably $C_{1-8}$alkoxy groups, more preferably $C_{1-6}$ alkoxy groups), cycloalkoxy groups ($C_{5-10}$ cycloalkoxy groups such as cyclohexyloxy groups), aryloxy groups ($C_{6-10}$ aryloxy groups such as phenoxy group), and aralkyloxy groups (for example, $C_{6-10}$ aryl $C_{1-4}$ alkyloxy groups such as benzyloxy group); groups represented by —$SR^{4b}$ wherein $R^{4b}$ represents a monovalent hydrocarbon group (for example, the above-exemplified monovalent hydrocarbon group) such as alkylthio groups (for example, $C_{1-12}$ alkylthio groups such as methylthio, ethylthio, propylthio, and butylthio groups, preferably $C_{1-8}$ alkylthio groups, more preferably $C_{1-6}$ alkylthio groups), cycloalkylthio groups (for example, $C_{5-10}$ cycloalkylthio groups such as cyclohexylthio groups), aryl thio groups ($C_{6-10}$ aryl thio groups such as phenylthio), and aralkyl thio groups (for example, $C_{6-10}$ aryl $C_{1-4}$ alkylthio groups such as benzylthio groups); acyl groups ($C_{1-6}$ acyl groups such as acetyl group); alkoxycarbonyl groups (for example, $C_{1-4}$ alkoxycarbonyl groups such as methoxycarbonyl group); halogen atoms (for example, a fluorine atom, a chlorine atom, a bromine atom, and an iodine atom); nitro group; cyano group; mercapto group; carboxyl group; amino group; carbamoyl group; groups represented by —$NHR^{4c}$ wherein $R^{4c}$ represents a monovalent hydrocarbon group (for example, the above-exemplified monovalent hydrocarbon group) such as alkylamino groups ($C_{1-12}$ alkylamino groups such as methylamino group, ethylamino group, propylamino group, and butylamino group, preferably $C_{1-8}$ alkylamino groups, more preferably $C_{1-6}$ alkylamino groups), cycloalkylamino groups (for example, $C_{5-10}$ cycloalkylamino groups such as cyclohexylamino group), arylamino groups ($C_{6-10}$ aryl amino groups such as phenylamino group), and aralkyl amino groups (for example, $C_{6-10}$ aryl $C_{1-4}$ alkylamino groups such as benzylamino group); groups represented by —$N(R^{4d})_2$ wherein $R^{4d}$ each independently represents a monovalent hydrocarbon group (for example, the above-exemplified monovalent hydrocarbon group) such as dialkylamino groups (di($C_{1-12}$ alkyl) amino groups such as dimethylamino group, diethylamino group, dipropylamino group, and dibutylamino group, preferably di($C_{1-8}$ alkyl)amino groups, more preferably di($C_{1-6}$ alkyl)amino groups), dicycloalkylamino groups (di($C_{5-10}$ cycloalkyl)amino groups such as dicyclohexylamino group), diaryl amino groups (di($C_{6-10}$ aryl)amino groups such as diphenylamino group), and diaralkyl amino groups (for example, di($C_{6-10}$ aryl $C_{1-4}$ alkyl)amino groups such as dibenzylamino group); (meth)acryloyloxy groups; sulfo group; and the above monovalent hydrocarbon groups, groups represented by —$OR^{4a}$, groups represented by —$SR^{4b}$, acyl groups, alkoxycarbonyl groups, groups represented by —$NHR^{4c}$, or groups formed by substituting at least a part of hydrogen atoms bonded to carbon atoms contained in groups represented by —$N(R^{4d})_2$ with the above monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group [for example, alkoxyaryl groups (for example, $C_{1-4}$ alkoxy $C_{6-10}$ aryl groups such as methoxyphenyl group), alkoxycarbonylaryl groups (for example, $C_{1-4}$ alkoxycarbonyl $C_{6-10}$ aryl groups such as methoxycarbonylphenyl group and ethoxycarbonylphenyl)].

Among them, typical examples of $R^2$ include monovalent hydrocarbon groups, groups represented by —$OR^{4a}$, groups represented by —$SR^{4b}$, acyl groups, alkoxycarbonyl groups, halogen atoms, nitro group, cyano group, groups represented by —$NHR^{4c}$, and groups represented by —$N(R^{4d})_2$.

Examples of preferred $R^2$ include monovalent hydrocarbon groups [for example, alkyl groups (for example, $C_{1-6}$ alkyl groups), cycloalkyl groups (for example, $C_{5-8}$ cycloalkyl groups), aryl groups (for example, $C_{6-10}$ aryl groups), and aralkyl groups (for example, $C_{6-8}$ aryl $C_{1-2}$ alkyl groups)], and alkoxy groups (for example, $C_{1-4}$ alkoxy groups). In particular, preferably, $R^{2a}$ and $R^{2b}$ represent a monovalent hydrocarbon group such as an alkyl group [for example, a $C_{1-4}$ alkyl group (particularly a methyl group)], an aryl group [for example, a $C_{6-10}$ aryl group (particularly a phenyl group)] (particularly an alkyl group).

When m is an integer of 2 or more, $R^2$'s may be different from or the same as each other. When both $W^1$ and $W^2$ represent a group represented by the general formula (2), or when one of $W^1$ and $W^2$ represents a group represented by the general formula (2) while the other represents a group represented by the general formula (4), $R^2$ contained in $W^1$ may be the same as or different from $R^2$ contained in $W^2$.

In the general formulae (2) and (4), the number of $R^2$'s, that is, m, may be selected according to the type of the ring Z and may be, for example, 0 to 4, preferably 0 to 3, more preferably 0 to 2. When both $W^1$ and $W^2$ represent a group represented by the general formula (2), or when one of $W^1$ and $W^2$ represents a group represented by the general formula (2) while the other represents a group represented by the general formula (4), m in $W^1$ may be the same as or different from m in $W^2$.

In the general formula (1), general examples of $R^{3a}$ and $R^{3b}$ include nonreactive substituents, for example, cyano group, halogen atoms (for example, fluorine atom, chlorine atom, and bromine atom), monovalent hydrocarbon groups [for example, alkyl groups and aryl groups ($C_{6-10}$ aryl groups such as phenyl group]. A cyano group or an alkyl group is preferred, and an alkyl group is particularly preferred. Examples of alkyl groups include $C_{1-6}$ alkyl groups (for example, $C_{1-4}$ alkyl groups, particularly methyl group) such as methyl, ethyl, propyl, isopropyl, butyl, and t-butyl groups. When n1 is an integer of 2 or more, $R^{3a}$'s may be the same as or different from each other. When n2 is an integer of 2 or more, $R^{3b}$'s may be the same as or different from each other. Further, $R^{3a}$ and $R^{3b}$ may be the same as or different from each other. The position of bonding of $R^{3a}$ and $R^{3b}$ to the benzene ring constituting fluorene (position of substitution) is not particularly limited. The number of substituents n1 and n2 is preferably 0 (zero) or 1, particularly preferably 0 (zero). n1 and n2 may be the same as or different from each other.

Compounds represented by the general formula (1) holds excellent optical properties and thermal properties characteristic of compounds having a fluorene skeleton and, at the same time, have a high reactivity by virtue of the presence of a vinyloxy group and/or a (meth)acryloyloxy group. The compounds represented by the general formula (1) can be polymerized and thus function as polymerizable monomers. In particular, when both $W^1$ and $W^2$ represent a group represented by the general formula (2), the compounds represented by the general formula (1) can be cationically polymerized and thus can function as cationically polymerizable monomers. On the other hand, when both $W^1$ and $W^2$ represent a (meth)acryloyloxy group, the compounds represented by the general formula (1) can be radically polymerized and thus function as radically polymerizable monomers. In the compounds represented by the general formula (1), when $W^1$ and $W^2$ each independently represent a group represented by the general formula (2) or a (meth)acryloyloxy group, two vinyl groups contained in the form of the vinyloxy group and/or the (meth)acryloyloxy group can be reacted with different molecules and, thus, the compounds represented by the general formula (1) are suitable as crosslinking agents. Further, the compounds represented by the general formula (1) can provide cured products having a high hardness and are preferred as a base component in the composition. In addition, when compounds represented by the general formula (1) are contained in negative-type photosensitive resin compositions, good micropatterning properties can be obtained.

Among the compounds represented by the general formula (1), particularly preferred examples thereof include compounds represented by the following formulae.

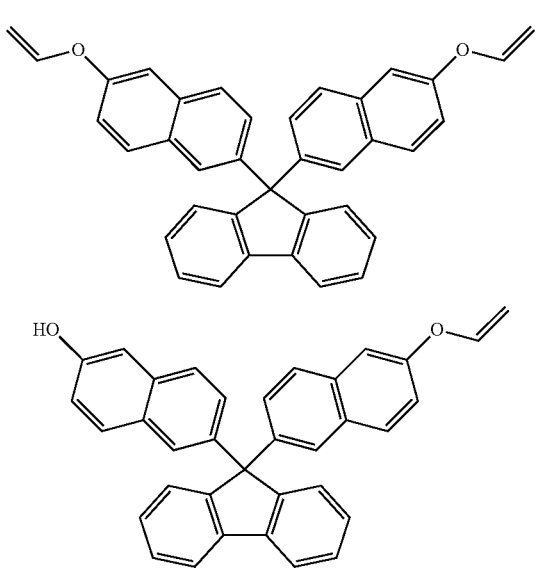

-continued

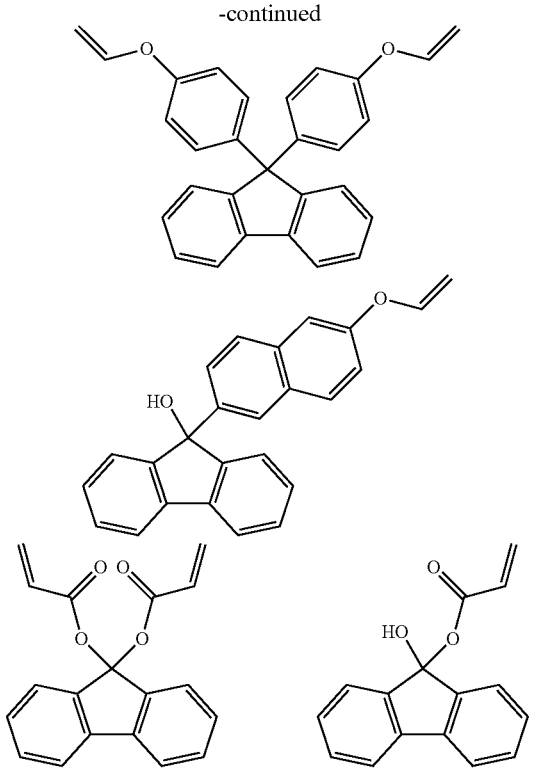

Process for Producing Vinyl-Group-Containing Fluorene-Based Compounds Represented by General Formula (1a)

Among the vinyl-group-containing fluorene-based compounds represented by the general formula (1), compounds represented by the general formula (1a) can be produced by the following production processes 1 to 3.

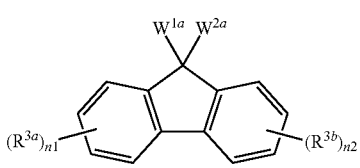                                                            (1a)

wherein $W^{1a}$ and $W^{2a}$ each independently represent a group represented by the general formula (2), a group represented by the general formula (4), a hydroxyl group, or a (meth) acryloyloxy group, provided that $W^{1a}$ and $W^{2a}$ do not simultaneously represent a hydroxyl group or a group represented by the general formula (4) or a (meth)acryloyloxy group; and $R^{3a}$, $R^{3b}$, n1, and n2 are as defined above.

Production Process 1

Vinyl-group-containing fluorene-based compounds represented by the general formula (1a) can be synthesized, for example, according to a production process described in JP2008-266169A by reacting a vinyl ester compound represented by the general formula (13) with a hydroxyl group-containing fluorene-based compound represented by the general formula (3) in the presence of a transition element compound catalyst and an inorganic base. The inorganic base is preferably a solid inorganic base containing not less than 10% by weight of particles having a diameter of less than 150 μm. Specifically, vinyl-group-containing fluorene-based compounds represented by the general formula (1a) can be synthesized as described in Synthesis Examples 1 to 3 that will be described later.

$$R^6\text{—CO—O—CH=CH}_2 \quad (13)$$

wherein $R^6$ represents a hydrogen atom or an organic group.

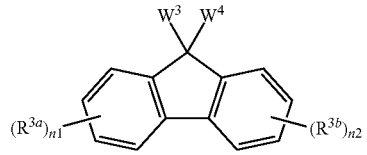                                                            (3)

wherein $W^3$ and $W^4$ each independently represent a group represented by the following general formula (4) or a hydroxyl group, provided that $W^3$ and $W^4$ do not simultaneously represent a hydroxyl group; and $R^{3a}$, $R^{3b}$, n1, and n2 are as defined above, and

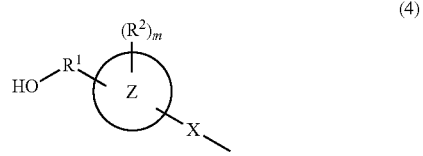                                                            (4)

wherein a ring Z, X, $R^1$, $R^2$, and m are as defined above.

Compounds represented by the general formula (3) can be synthesized, for example, by reacting a compound represented by the following general formula (14) and/or a compound represented by the following general formula (15) with a compound represented by the general formula (16) in the presence of an acid catalyst. Desired hydroxyl group-containing fluorene-based compounds represented by the general formula (3) can be obtained by properly regulating a combination of compounds represented by the general formula (14) and compounds represented by the general formula (15) and the addition amounts of the compounds. After the reaction, contemplated hydroxyl group-containing fluorene-based compounds may be separated by publicly known separation methods, for example, column chromatography on silica gel.

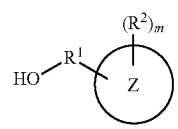                                                            (14)

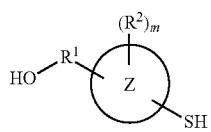                                                            (15)

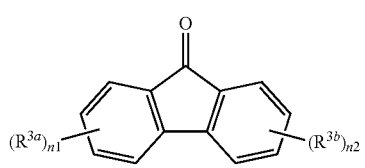                                                            (16)

wherein, in the general formulae (14), (15), and (16), a ring Z, $R^1$, $R^2$, $R^{3a}$, $R^{3b}$, m, n1, and n2 are as defined above.

Acid catalysts usable in the synthesis of compounds represented by the general formula (3), reaction condition and the like may be those that are described in Patent Literature 1 or JP2002-255929A to the effect that are used in the production process of fluorene-based compounds described in claims.

Production Process 2

Compounds represented by the general formula (1a) can also be synthesized by a production process that includes obtaining vinyl-group-containing fluorene-based compounds represented by the general formula (1a) from hydroxyl group-containing fluorene-based compounds represented by the general formula (3) through leaving group-containing fluorene-based compounds represented by the general formula (5).

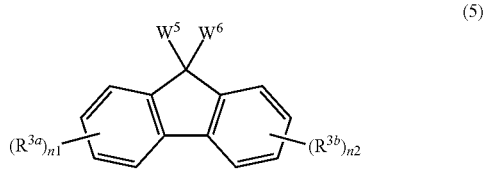

(5)

wherein $W^5$ and $W^6$ each independently represent a group represented by the general formula (6) or a hydroxyl group, provided that $W^5$ and $W^6$ do not simultaneously represent a hydroxyl group; and $R^{3a}$, $R^{3b}$, n1, and n2 are as defined above, and

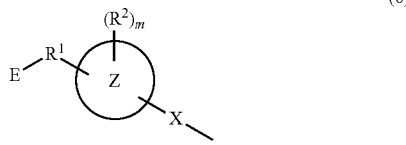

(6)

wherein E represents an alkyloxy group having 1 to 4 carbon atoms substituted by a chlorine atom, a bromine atom, an iodine atom, a methanesulfonyloxy group, a trifluoromethanesulfonyloxy group, a p-toluenesulfonyloxy group, or a benzenesulfonyloxy; and a ring Z, X, $R^1$, $R^2$, and m are as defined above.

Leaving group-containing fluorene-based compounds represented by the general formula (5) can be synthesized, for example, by reacting hydroxyl group-containing fluorene-based compounds represented by the general formula (3) with leaving group-containing compounds. Leaving group-containing compounds include, for example, thionyl chloride, compounds represented by the following formula. The temperature of the reaction may be, for example, −20 to 150° C., preferably −10 to 140° C., more preferably 30 to 130° C.

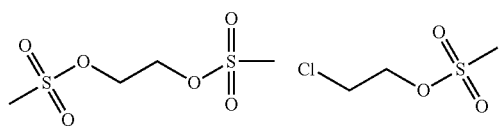

Vinyl-group-containing fluorene-based compounds represented by the general formula (1a) can be synthesized, for example, by reacting leaving group-containing fluorene-based compounds represented by the general formula (5) with vinylating agents. Vinylating agents include, for example, sodium hydroxide, triethylamine, diisopropyl ethylamine, 1,4-diazabicyclo[2.2.2]octane, diazabicyclo undecene, sodium methoxide, sodium ethoxide, sodium ethoxide, and potassium t-butoxide. Preferred are diazabicyclo undecene, sodium ethoxide, and potassium t-butoxide. More preferred is potassium t-butoxide. The temperature of the reaction is, for example, −20 to 150° C., preferably −10 to 100° C., more preferably 0 to 60° C.

Production Process 3

Compounds represented by the general formula (1a) can also be synthesized, for example, by a production process that includes obtaining vinyl-group-containing fluorene-based compounds represented by the general formula (1a) from hydroxyalkyloxy group-containing fluorene-based compounds represented by the general formula (7) through leaving group-containing fluorene-based compounds represented by the general formula (5). Specifically, compounds represented by the general formula (1a) can be synthesized as described in Synthesis Examples 4 and 5 and Synthesis Examples 12 and 13.

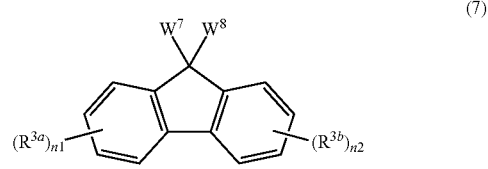

(7)

wherein $W^7$ and $W^8$ each independently represent a group represented by the general formula (8) or a hydroxyl group, provided that $W^7$ and $W^8$ do not simultaneously represent a hydroxyl group; and $R^{3a}$, $R^{3b}$, n1, and n2 are as defined above, and

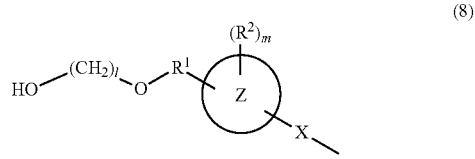

(8)

wherein l represents an integer of 1 to 4; and a ring Z, X, $R^1$, $R^2$, and m are as defined above.

Hydroxyalkyloxy group-containing fluorene-based compounds represented by the general formula (7) can be synthesized, for example, by reacting compounds represented by the following general formula (17) and/or compounds represented by the following general formula (18) with compounds represented by the general formula (16) in the presence of an acid catalyst. Desired hydroxyalkyloxy group-containing fluorene-based compounds represented by the general formula (7) can be obtained by properly regulating a combination of compounds represented by the following general formula (17) and compounds represented by the following general formula (18) and the addition amounts of the compounds. After the reaction, contemplated hydroxyalkyloxy group-containing fluorene-based compounds may be separated, for example, by publicly known separation methods such as column chromatography on silica gel. Acid catalysts, reaction conditions and the like usable in the synthesis of compounds represented by the general formula (7) may be, for example, those that are exemplified in the description of the synthesis method of compounds represented by the general formula (3).

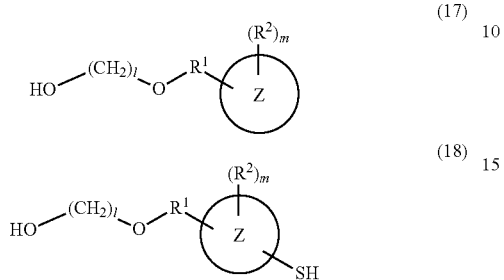

(17)

(18)

wherein, in the general formulae (17) and (18), a ring Z, $R^1$, $R^2$, and m are as defined above.

Leaving group-containing fluorene-based compounds represented by the general formula (5) can be synthesized, for example, by reacting hydroxyalkyloxy group-containing fluorene-based compounds represented by the general formula (7) with leaving group-containing compounds. The leaving group-containing compound and the reaction temperature may be those that are exemplified in the description of the production process 2.

Vinyl-group-containing fluorene-based compounds represented by the general formula (1a) can be synthesized, for example, by reacting leaving group-containing fluorene-based compounds represented by the general formula (5) with vinylating agents. The vinylating agent and the reaction temperature may be, for example, those that are exemplified in the production process 2.

According to the production process 3, compounds represented by the general formula (1a) can be obtained from hydroxyalkyloxy group-containing fluorene-based compounds represented by the general formula (7) at a high yield. For example, the yield of 9,9'-bis(6-vinyloxy-2-naphthyl)fluorene was 77% in Synthesis Examples 4 and 5, and the yield of 9,9'-bis(4-vinyloxyphenyl)fluorene was 79% in Synthesis Examples 12 and 13. According to the production process 3, the load in the step of purification of compounds represented by the general formula (1a) can be reduced. Further, in the production process 3, the reaction can be carried out at ordinary pressures, and, thus, special reaction facilities such as heat-resistant vessels are unnecessary, making it possible to use simpler apparatuses. Further, in the production process 3, flammable gases such as acetylene gas are not used, and, thus, compounds represented by the general formula (1a) can be produced more safely.

Leaving Group-Containing Fluorene-Based Compounds Represented by General Formula (5)

Leaving group-containing fluorene-based compounds according to the present invention are represented by the general formula (5). The leaving group-containing fluorene-based compounds are useful as intermediates for the production of vinyl-group-containing fluorene-based compounds represented by the general formula (1a). Leaving group-containing fluorene-based compounds represented by the general formula (5) can be synthesized, for example, by methods described in the production process 2 or 3.

Monovinyl-Group-Containing Fluorene-Based Compounds Represented by General Formula (9) and Production Process Thereof Monovinyl-group-containing fluorene-based compounds according to the present invention are represented by the following general formula (9). The monovinyl-group-containing fluorene-based compounds are useful as intermediates for the production of vinyl-group-containing fluorene-based compounds represented by the general formula (1a).

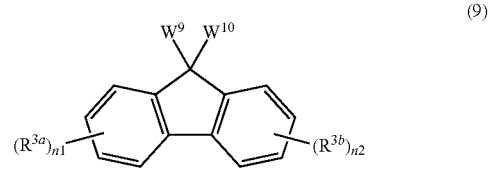

(9)

wherein any one of $W^9$ and $W^{10}$ represent a group represented by the general formula (2) while the other represents a group represented by the general formula (6); and $R^{3a}$, $R^{3b}$, n1, and n2 are as defined above.

Monovinyl-group-containing fluorene-based compounds represented by the general formula (9) can be synthesized by a production process that includes monovinyl-group-containing fluorene-based compounds represented by the general formula (9) from leaving group-containing fluorene-based compounds represented by the general formula (5a). Specifically, monovinyl-group-containing fluorene-based compounds represented by the general formula (9) can be synthesized as described in Synthesis Examples 8 and 11 that will be described later. That is, monovinyl-group-containing fluorene-based compounds represented by the general formula (9) can be synthesized, for example, by reacting leaving group-containing fluorene-based compounds represented by the following general formula (5a) with vinylating agents. The vinylating agent and the reaction temperature may be, for example, those that are exemplified in the production process 2. The amount of the vinylating agent used is preferably 0.1 to 10 moles, more preferably 0.5 to 5 moles, still more preferably 0.8 to 2 moles per mole of the leaving group in the leaving group-containing fluorene-based compound represented by the following general formula (5a).

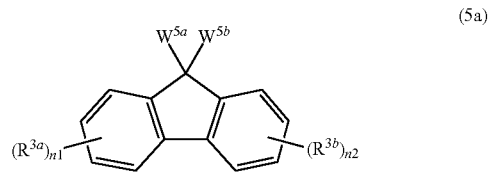

(5a)

wherein $W^{5a}$ and $W^{6a}$ represent a group represented by the general formula (6); and $R^{3a}$, $R^{3b}$, n1, and n2 are as defined above.

Monovinyl group- and mono(meth)acryloyloxy group-containing fluorene-based compounds represented by general formula (10)

Monovinyl group- and mono(meth)acryloyloxy group-containing fluorene-based compounds according to the present invention are represented by the general formula (10). The compounds have a high reactivity by virtue of the presence of the vinyloxy group and the (meth)acryloyloxy group while maintaining excellent optical properties and thermal properties characteristic of compounds having a fluorene skeleton. As with vinyl-group-containing fluorene-based compounds represented by the general formula (1), compounds represented by the following general formula (10) can be polymerized and thus function as polymerizable monomers and are suitable as crosslinking agents. Further, compounds represented by the general formula (10) can provide cured products having a high hardness and thus are preferred as a base component in the composition. In addition, when compounds represented by the general formula (10) are incorporated in negative-type photosensitive resin compositions, good micropatterning properties can be obtained.

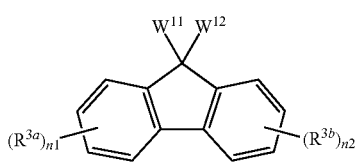
(10)

wherein any one of $W^{11}$ and $W^{12}$ represents a group represented by the general formula (2) while the other represents a group represented by the following general formula (11) or (12); and $R^{3a}$, $R^{3b}$, n1, and n2 are as defined above,

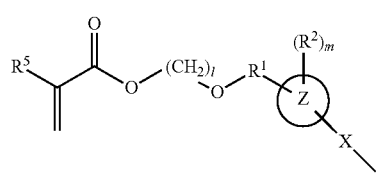
(11)

wherein $R^5$ represents a hydrogen atom or a methyl group; and a ring Z, X, $R^1$, $R^2$, m, and l are as defined above, and

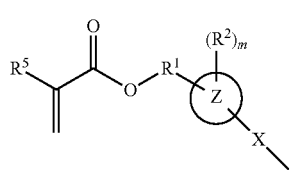
(12)

wherein a ring Z, X, $R^1$, $R^2$, $R^5$, and m are as defined above.
(Meth)acryloyloxy group-containing fluorene-based compounds represented by the general formula (19)

(Meth)acryloyloxy group-containing fluorene-based compounds according to the present invention are represented by the general formula (19). The compounds have a high reactivity by virtue of the presence of the (meth)acryloyloxy group while maintaining excellent optical properties and thermal properties characteristic of compounds having a fluorene skeleton. As with vinyl-group-containing fluorene-based compounds represented by the general formula (1), compounds represented by the following general formula (19) can be polymerized and thus function as polymerizable monomers and are suitable as crosslinking agents. Further, compounds represented by the following general formula (19) can provide cured products having a high hardness and are preferred as a base component in the composition. In addition, when compounds represented by the following general formula (19) are incorporated in negative-type photosensitive resin compositions, good micropatterning properties can be obtained.

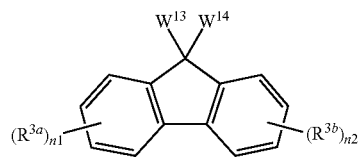
(19)

wherein $W^{13}$ and $W^{14}$ each independently represent a group represented by the general formula (12), a hydroxyl group, or a (meth)acryloyloxy group, provided that at least one of $W^{13}$ and $W^{14}$ represent a group represented by the general formula (12); and $R^{3a}$, $R^{3b}$, n1, and n2 are as defined above.

Among compounds represented by the general formula (19), specific examples of particularly preferred compounds include compounds represented by the following formulae.

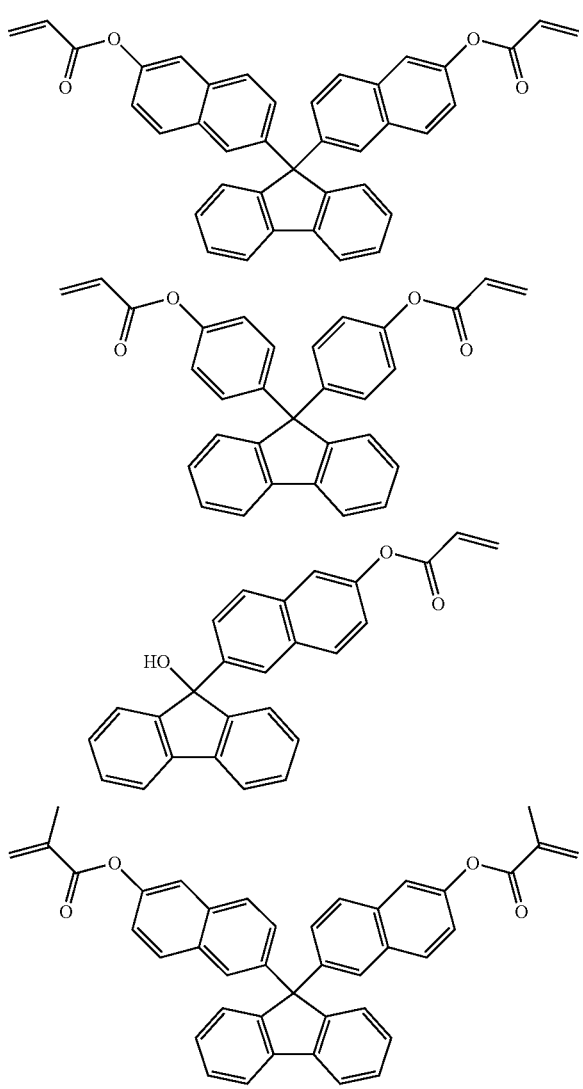

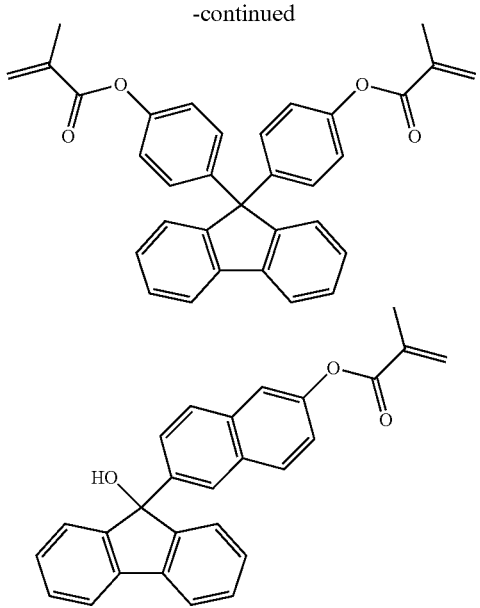

Production Process of (Meth)Acryloyloxy Group-Containing Fluorene-Based Compounds Represented by General Formula (19)

Compounds represented by the general formula (19) can be synthesized, for example, by a production process that includes obtaining (meth)acryloyloxy group-containing fluorene-based compound represented by the general formula (19) from hydroxyl group-containing fluorene-based compounds represented by the general formula (3). Specifically, compounds represented by the general formula (19) can be synthesized as described in Synthesis Examples 14 and 15 that will be described later Compounds represented by the general formula (19) can be synthesized, for example, by reacting hydroxyl group-containing fluorene-based compounds represented by the general formula (3) with (meth)acrylating agents. Examples of (meth)acrylating agents include (meth)acryloyl halides such as (meth)acryloyl chlorides; and (meth)acrylic anhydrides. Preferred are (meth)acryloyl halides. More preferred are (meth)acryloyl chlorides. The reaction temperature may be, for example, −20 to 150° C., preferably −10 to 100° C., more preferably 0 to 60° C. The term "(meth)acrylating agent" as used herein refers to both acrylating agents and methacrylating agents, and the term "(meth)acrylic anhydride" refers to both acrylic anhydride and methacrylic anhydride.

Negative-Type Photosensitive Resin Composition

As described above, compounds represented by the general formula (1), compounds represented by the general formula (10), and compounds represented by the general formula (19) are useful as ingredients in negative-type photosensitive resin compositions. An example of the negative-type photosensitive resin compositions is one including an alkali-soluble resin, a photopolymerizable monomer, a photopolymerization initiator, a compound represented by the general formula (1), a compound represented by the general formula (10) and/or a compound represented by the general formula (19), and an organic solvent. The negative-type photosensitive resin composition will be described in detail.

As the alkali-soluble resin contained in the negative-type photosensitive resin composition, conventional publicly known alkali-soluble resins are usable without particular limitation. The alkali-soluble resin may be the one which has an ethylenic unsaturated group or the one which does not have any ethylenic unsaturated group.

In the present specification, the term "alkali-soluble resin" means that, in the case where a resin film having a film thickness of 1 μm is formed on a substrate by using a resin solution (solvent: propylene glycol monomethyl ether acetate) having a resin concentration of 20 mass %, a film thickness of 0.01 μm or more is dissolved when the substrate is immersed in a 2.38 mass % tetramethyl ammonium hydroxide (TMAH) aqueous solution for 1 minute.

As the alkali-soluble resin having ethylenic unsaturated group, for example, resins obtainable by causing a reaction of a reaction product of an epoxy compound and unsaturated carboxylic acid with a polybasic acid anhydride are usable.

Among them, the resin represented by the following formula (r-1) is preferred. The resin represented by the formula (r-1) is preferred since the resin itself has high photo-curability.

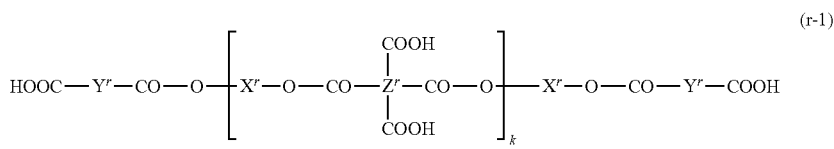

(r-1)

such as (meth)acryloyl chlorides; and (meth)acrylic anhydrides. Preferred are (meth)acryloyl halides. More preferred In the above formula (r-1), $X^r$ indicates a group represented by the following formula (r-2).

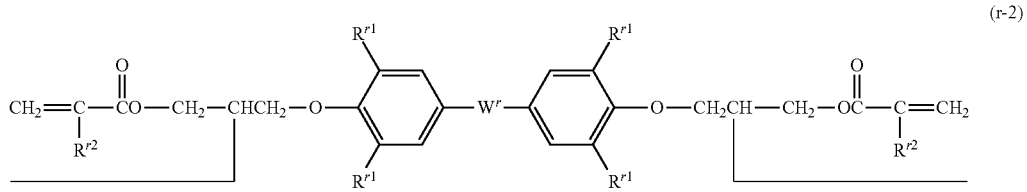

(r-2)

In the general formula (r-2), $R^{r1}$ each independently indicates a hydrogen atom, a hydrocarbon group having 1 to 6 carbon atoms, or a halogen atom; $R^{r2}$ each independently indicates a hydrogen atom or a methyl group; and $W^r$ indicates a single bond or a group represented by the following formula (r-3).

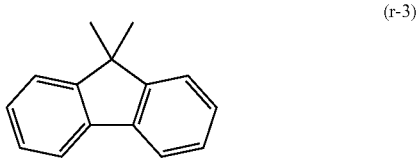

(r-3)

Also, in the formula (r-1), $Y^r$ indicates a residue obtainable by removing an acid anhydride group (—CO—O—CO—) from dicarboxylic anhydride. Examples of the dicarboxylic anhydride include maleic anhydride, succinic anhydride, itaconic anhydride, phthalic anhydride, tetrahydrophthalic anhydride, hexahydrophthalic anhydride, methylendomethylenetetrahydrophthalic anhydride, chlorendic anhydride, methyltetrahydrophthalic anhydride, anhydrous glutaric acid, and the like.

In the formula (r-1), $Z^r$ indicates a residue obtainable by removing 2 acid anhydride groups from tetracarboxylic acid dianhydride. Examples of the tetracarboxylic acid dianhydride include pyromellitic dianhydride, benzophenonetetracarboxylic dianhydride, biphenyltetracarboxylic dianhydride, biphenylethertetracarboxylic dianhydride, and the like.

In the formula (r-1), k indicates an integer of 0 to 20.

As the alkali-soluble resin having ethylenic unsaturated group, polyester(meth)acrylate obtainable by causing a reaction of a polyester prepolymer obtained by condensation of polyvalent alcohols with monobasic acid or polybasic acid with (meth)acrylic acid; polyurethane(meth)acrylate obtainable by causing a reaction of polyol with a compound having 2 isocyanate groups and then performing a reaction with (meth)acrylic acid; an epoxy(meth)acrylate resin obtainable by causing a reaction of an epoxy resin such as a bisphenol A-type epoxy resin, a bisphenol F-type epoxy resin, a bisphenol S-type epoxy resin, a phenol or cresol novolac-type epoxy resin, a resol-type epoxy resin, a triphenolmethane-type epoxy resin, polycarboxylic acid polyglycidyl ester, polyol polyglycidyl ester, an aliphatic or alicyclic epoxy resin, an amine epoxy resin, and a dihydroxybenzene-type epoxy resin with (meth)acrylic acid may be used.

The term "(meth)acrylic acid" as used herein means both acrylic acid and methacrylic acid. Likewise, the term "(meth)acrylate" means both acrylate and methacrylate. Further, "(meth)acrylamide" means both acrylamide and methacrylamide.

As the alkali-soluble resin which does not have any ethylenic unsaturated group, a resin which is obtainable by copolymerizing at least an unsaturated carboxylic acid, an epoxy group-containing unsaturated compound which does not have any alicyclic group, and an alicyclic group-containing unsaturated compound may be used.

Examples of the unsaturated carboxylic acid include monocarboxylic acid such as (meth)acrylic acid and crotonic acid; dicarboxylic acid such as maleic acid, fumaric acid, citraconic acid, mesaconic acid, and itaconic acid; anhydrides of these dicarboxylic acids; and the like. Among these, (meth)acrylic acid and maleic anhydride are preferred from the viewpoints of copolymerization reactivity, alkali solubility of the obtained resin, easy availability, and so forth. These unsaturated carboxylic acids may be used alone or in combination of two or more kinds thereof.

Examples of the epoxy group-containing unsaturated compound which does not have any alicyclic group include (meth)acrylic acid epoxyalkyl esters such as glycidyl(meth)acrylate, 2-methylglycidyl(meth)acrylate, 3,4-epoxybutyl (meth)acrylate, 6,7-epoxyheptyl(meth)acrylate, 3,4-epoxycyclohexyl(meth)acrylate; α-alkylacrylic acid epoxyalkyl esters such as glycidyl α-ethylacrylate, glycidyl α-n-propylacrylate, glycidyl α-n-butylacrylate, and 6,7-epoxyheptyl α-ethylacrylate; glycidyl ethers such as o-vinylbenzyl glycidyl ether, m-vinylbenzyl glycidyl ether, and p-vinylbenzyl glycidyl ether; and the like. Among these, glycidyl(meth)acrylate, 2-methylglycidyl(meth)acrylate, 6,7-epoxyheptyl (meth)acrylate, o-vinylbenzyl glycidyl ether, m-vinylbenzyl glycidyl ether and p-vinylbenzyl glycidyl ether are preferred from the viewpoints of copolymer reactivity, resin strength after curing and so forth. These epoxy group-containing unsaturated compounds may be used alone or in combination of two or more kinds thereof.

As the alicyclic group-containing unsaturated compound, an unsaturated compound may be used without particular limitation insofar as the unsaturated compound has an alicyclic group. The alicyclic group may be monocyclic or polycyclic. Examples of monocyclic alicyclic group include a cyclopentyl group, a cyclohexyl group, and the like. Examples of the polycyclic alicyclic group include an adamantyl group, a norbornyl group, an isobornyl group, a tricyclononyl group, a tricyclodecyl group, a tetracyclodecyl group, and the like. More specifically, examples of the alicyclic group-containing unsaturated compound include the compounds represented by the following formula.

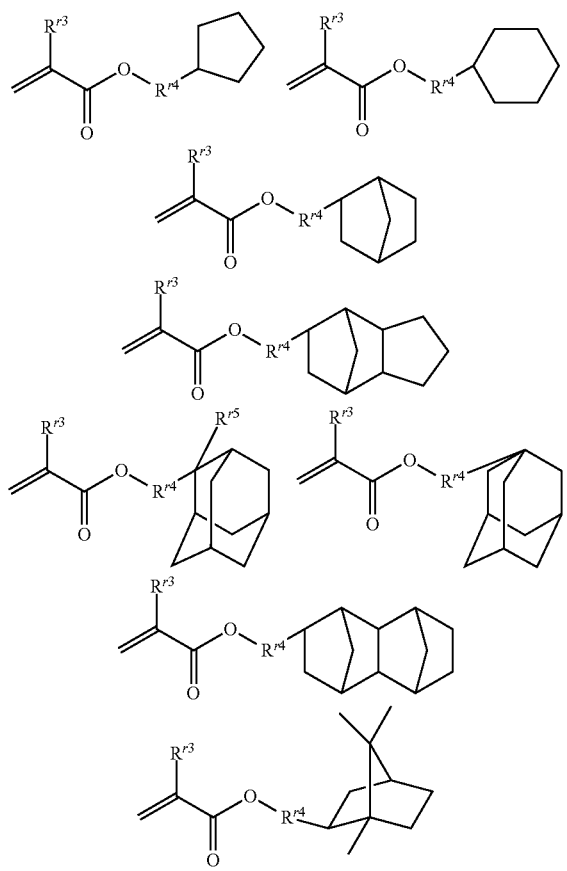

In the above formula, $R^{r3}$ indicates a hydrogen atom or a methyl group; $R^{r4}$ indicates a single bond or a divalent aliphatic saturated hydrocarbon group having 1 to 6 carbon atoms; and $R^{r5}$ indicates a hydrogen atom or an alkyl group having 1 to 5 carbon atoms. As the $R^{r4}$, a single bond, a straight chain or branched chain alkylene group such as a methylene group, an ethylene group, a propylene group, a tetramethylene group, an ethylethylene group, a pentamethylene group, and a hexamethylene group are preferred. As the $R^{r5}$, a methyl group and an ethyl group are preferred.

In the alkali-soluble resin, a ratio of a constitutional unit derived from the unsaturated carboxylic acid is preferably 3 to 25 mass %, more preferably 5 to 25 mass %. Also, a ratio of a constitutional unit derived from the epoxy group-containing unsaturated compound is preferably 71 to 95 mass %, more preferably 75 to 90 mass %. Also, a ratio of a constitutional unit derived from the alicyclic group-containing unsaturated compound is preferably 1 to 25 mass %, more preferably 3 to 20 mass %, further preferably 5 to 15 mass %. With the above-specified ranges, it is possible to enhance the adhesiveness of the negative-type photosensitive resin composition to substrates and the strength of the negative-type photosensitive resin composition after curing while maintaining alkali solubility of the obtained resin at an appropriate level.

A mass average molecular weight of the alkali-soluble resin is preferably 1000 to 40000, more preferably 2000 to 30000. With the above-specified range, it is possible to attain satisfactory heat resistance and film strength while attaining favorable developability.

A content of the alkali-soluble resin is preferably 5 to 80 mass %, more preferably 15 to 50 mass %, relative to a solid content of the negative-type photosensitive resin composition. With the above-specified range, there is a tendency that developability is well-balanced.

The photopolymerizable monomer to be contained in the negative-type photosensitive resin composition includes a monofunctional monomer and a multifunctional monomer.

Examples of the monofunctional monomer include (meth)acryl amide, methylol(meth)acrylamide, methoxymethyl(meth)acrylamide, ethoxymethyl(meth)acrylamide, propoxymethyl(meth)acrylamide, butoxymethoxymethyl(meth)acrylamide, N-methylol(meth)acrylamide, N-hydroxymethyl(meth)acrylamide, (meth)acrylic acid, fumaric acid, maleic acid, maleic anhydride, itaconic acid, itaconic anhydride, citraconic acid, citraconic anhydride, crotonic acid, 2-acrylamide-2-methylpropanesulfonic acid, tert-butylacrylamidesulfonic acid, methyl(meth)acrylate, ethyl(meth)acrylate, butyl(meth)acrylate, 2-ethylhexyl(meth)acrylate, cyclohexyl(meth)acrylate, 2-hydroxyethyl(meth)acrylate, 2-hydroxypropyl(meth)acrylate, 2-hydroxybutyl(meth)acrylate, 2-phenoxy-2-hydroxypropyl(meth)acrylate, 2-(meth)acryloyloxy-2-hydroxypropyl phthalate, glycerin mono(meth)acrylate, tetrahydrofurfuryl(meth)acrylate, dimethylamino(meth)acrylate, glycidyl(meth)acrylate, 2,2,2-trifluoroethyl(meth)acrylate, 2,2,3,3-tetrafluoropropyl(meth)acrylate, half(meth)acrylate of a phthalic acid derivative, and the like. These monofunctional monomers may be used alone or in combination of two or more kinds thereof.

Meanwhile, examples of the multifunctional monomer include ethylene glycol di(meth)acrylate, diethylene glycol di(meth)acrylate, tetraethylene glycol di(meth)acrylate, propylene glycol di(meth)acrylate, polypropylene glycol di(meth)acrylate, butylene glycol di(meth)acrylate, neopentyl glycol di(meth)acrylate, 1,6-hexane glycol di(meth)acrylate, trimethylolpropane tri(meth)acrylate, glycerin di(meth)acrylate, pentaerythritol triacrylate, pentaerythritol tetraacrylate, dipentaerythritol pentaacrylate, dipentaerythritol hexaacrylate, pentaerythritol di(meth)acrylate, pentaerythritol tri(meth)acrylate, pentaerythritol tetra(meth)acrylate, dipentaerythritol penta(meth)acrylate, dipentaerythritol hexa(meth)acrylate, 2,2-bis(4-(meth)acryloxydiethoxyphenyl)propane, 2,2-bis(4-(meth)acryloxypolyethoxyphenyl)propane, 2-hydroxy-3-(meth)acryloyloxypropyl(meth)acrylate, ethylene glycol diglycidyl ether di(meth)acrylate, diethylene glycol diglycidyl ether di(meth)acrylate, phthalic acid diglycidyl ester di(meth)acrylate, glycerin triacrylate, glycerin polyglycidyl ether poly(meth)acrylate, urethane (meth)acrylate (i.e. tolylene diisocyanate), a reaction product of trimethylhexamethylene diisocyanate, hexamethylene diisocyanate, and 2-hydroxyethyl(meth)acrylate, methylene bis(meth)acrylamide, (meth)acrylamide methylene ether, a multifunctional monomer such as a condensate of a polyvalent alcohol and N-methylol(meth)acrylamide, triacryl formal, and the like. These multifunctional monomers may be used alone or in combination of two or more kinds thereof.

A content of the photopolymerizable monomer is preferably 1 to 30 mass %, more preferably 5 to 20 mass %, relative to the solid content of the negative-type photosensitive resin composition. With the above-specified range, there is a tendency that sensitivity, developability, and resolution are well-balanced.

As the photopolymerization initiator to be contained in the negative-type photosensitive resin composition, conventionally known photopolymerization initiators are usable without particular limitation.

Specific examples of the photopolymerization initiator include 1-hydroxy-cyclohexylphenylketone, 2-hydroxy-2-methyl-1-phenylpropan-1-one, 1-[4-(2-hydroxyethoxy)phenyl]-2-hydroxy-2-methyl-1-propan-1-one, 1-(4-isopropylphenyl)-2-hydroxy-2-methylpropan-1-one, 1-(4-dodecylphenyl)-2-hydroxy-2-methylpropan-1-one, 2,2-dimethoxy-1,2-diphenylethan-1-one, bis(4-dimethylaminophenyl)ketone, 2-methyl-1-[4-(methylthio)phenyl]-2-morpholinopropan-1-one, 2-benzyl-2-dimethylamino-1-(4-morpholinophenyl)-butan-1-one, ethanone, 1-[9-ethyl-6-(2-methylbenzoyl)-9H-carbozol-3-yl], 1-(o-acetyloxime), 2,4,6-trimethylbenzoyldiphenylphosphineoxide, 4-benzoyl-4'-methyldimethylsulfide, 4-dimethylaminobenzoic acid, methyl 4-dimethylaminobenzoate, ethyl 4-dimethylaminobenzoate, butyl 4-dimethylaminobenzoate, 4-dimethylamino-2-ethylhexylbenzoic acid, 4-dimethylamino-2-isoamylbenzoic acid, benzyl-β-methoxyethylacetal, benzyldimethylketal, 1-phenyl-1,2-propanedione-2-(o-ethoxycarbonyl)oxime, methyl o-benzoylbenzoate, 2,4-diethylthioxanthone, 2-chlorothioxanthone, 2,4-dimethylthioxanthone, 1-chloro-4-propoxythioxanthone, thioxanthene, 2-chlorothioxanthene, 2,4-diethylthioxanthene, 2-methylthioxanthene, 2-isopropylthioxanthene, 2-ethylanthraquinone, octamethylanthraquinone, 1,2-benzanthraquinone, 2,3-diphenylanthraquinone, azobisisobutyronitrile, benzoyl peroxide, cumene peroxide, 2-mercaptobenzimidazole, 2-mercaptobenzoxazole, 2-mercaptobenzothiazole, 2-(o-chlorophenyl)-4,5-diphenylimidazole dimers, 2-(o-chlorophenyl)4,5-di(methoxyphenyl)imidazole dimers, 2-(o-fluorophenyl)-4,5-diphenylimidazole dimers, 2-(o-methoxyphenyl)-4,5-diphenylimidazole dimers, 2-(p-methoxyphenyl)-4,5-diphenylimidazole dimers, 2,4,5-triarylimidazole dimers, benzophenone, 2-chlorobenzophenone, 4,4'-bisdiethylaminobenzophenone (i.e. Michler's ketone), 4,4'-bisdiethylaminobenzophenone (i.e. ethyl Michler's ketone), 4,4'-dichlorobenzophenone, 3,3-dimethyl-4-methoxybenzophenone, benzyl, benzoin, benzoin methyl ether, benzoin ethyl ether, benzoin isopropyl ether, benzoin-n-butyl ether, benzoin isobutyl ether, benzoin butyl ether, acetophenone, 2,2-diethoxyacetophenone, p-dimethylacetophenone, p-dimethylaminopropiophenone, dichloroacetophenone, trichloroacetophenone, p-tert-butylacetophenone, p-dimethylaminoacetophenone, p-tert-butyltrichloroacetophenone, p-tert-butyldichloroacetophenone, α,α-dichloro-4-phenoxyacetophenone, thioxanthone, 2-methylthioxanthone, 2-isopropylthioxanthone, dibenzosuberone, pentyl-4-dimethylamino benzoate, 9-phenylacridine, 1,7-bis-(9-acridinyl)heptane, 1,5-bis-(9-acridinyl)pentane, 1,3-bis-(9-acridinyl)propane, p-methoxytriazine, 2,4,6-tris(trichloromethyl)-s-triazine, 2-methyl-4,6-bis(trichloromethyl)-s-triazine, 2-[2-(5-methylfuran-2-yl) ethenyl]-4,6-bis(trichloromethyl)-s-triazine, 2-[2-(furan-2-yl)ethenyl-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl) ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, 2-(4-n-butoxyphenyl)-4,6-bis(trichloromethyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(3-bromo-4-methoxy) styrylphenyl-s-triazine, 2,4-bis-trichloromethyl-6-(2-bromo-4-methoxy)styrylphenyl-s-triazine, and the like. Among these, it is particularly preferable to use the oxime-based photopolymerization initiator from the viewpoint of sensitivity. These photopolymerization initiators may be used alone or in combination of two or more kinds thereof.

A content of the photopolymerization initiator is preferably 0.5 to 20 parts by mass relative to 100 parts by mass of the solid content of the negative-type photosensitive resin composition. With the above-specified range, it is possible to attain satisfactory heat resistance and chemical resistance and to suppress a curing defect by improving coating film formation capability.

The negative-type photosensitive resin composition contains the compound represented by the general formula (1), the compound represented by the general formula (10), and/or the compound represented by the general formula (19). When the compounds are contained in the negative-type photosensitive resin composition, good micropatterning properties can be obtained.

The content of the compound represented by the general formula (1), the compound represented by the general formula (10), and/or the compound represented by the general formula (19) is preferably 0.5 to 95 parts by mass, more preferably 1 to 50 parts by mass, based on 100 parts by mass of the photopolymerization initiator. With the above-specified range, it is possible to attain a favorable micropatterning property while attaining favorable developability.

The negative-type photosensitive resin composition may further comprise a coloring agent. When the coloring agent is contained, the negative-type photosensitive resin composition is favorably used for forming a color filter of liquid crystal displays, for example. Also, when the negative-type photosensitive resin composition contains a light shielding agent as the coloring agent, it is favorably used for forming a black matrix in the color filter, for example.

The coloring agent is not particularly limited, but it is preferable to use, for example, compounds which are classified into Pigment in Color Index (C.I.; published by The Society of Dyers and Colorist), and specifically those having the following color index (C.I.) numbers.

C.I. pigment yellow 1 (hereinafter, "C.I. pigment yellow" is omitted, and only the numbers are listed), 3, 11, 12, 13, 14, 15, 16, 17, 20, 24, 31, 53, 55, 60, 61, 65, 71, 73, 74, 81, 83, 86, 93, 95, 97, 98, 99, 100, 101, 104, 106, 108, 109, 110, 113, 114, 116, 117, 119, 120, 125, 126, 127, 128, 129, 137, 138, 139, 147, 148, 150, 151, 152, 153, 154, 155, 156, 166, 167, 168, 175, 180, and 185;

C.I. pigment orange 1 (hereinafter, "C.I. pigment orange" is omitted, and only the numbers are listed), 5, 13, 14, 16, 17, 24, 34, 36, 38, 40, 43, 46, 49, 51, 55, 59, 61, 63, 64, 71, and 73;

C.I. pigment violet 1 (hereinafter, "C.I. pigment violet" is omitted, and only the numbers are listed), 19, 23, 29, 30, 32, 36, 37, 38, 39, 40, and 50;

C.I. pigment red 1 (hereinafter, "C.I. pigment red" is omitted, and only the numbers are listed), 2, 3, 4, 5, 6, 7, 8, 9, 10, 11, 12, 14, 15, 16, 17, 18, 19, 21, 22, 23, 30, 31, 32, 37, 38, 40, 41, 42, 48:1, 48:2, 48:3, 48:4, 49:1, 49:2, 50:1, 52:1, 53:1, 57, 57:1, 57:2, 58:2, 58:4, 60:1, 63:1, 63:2, 64:1, 81:1, 83, 88, 90:1, 97, 101, 102, 104, 105, 106, 108, 112, 113, 114, 122, 123, 144, 146, 149, 150, 151, 155, 166, 168, 170, 171, 172, 174, 175, 176, 177, 178, 179, 180, 185, 187, 188, 190, 192, 193, 194, 202, 206, 207, 208, 209, 215, 216, 217, 220, 223, 224, 226, 227, 228, 240, 242, 243, 245, 254, 255, 264, and 265;

C.I. pigment blue 1 (hereinafter, "C.I. pigment blue" is omitted, and only the numbers are listed), 2, 15, 15:3, 15:4, 15:6, 16, 22, 60, 64, and 66;

C.I. pigment green 7, C.I. pigment green 36, and C.I. pigment green 37;

C.I. pigment brown 23, C.I. pigment brown 25, C.I. pigment brown 26, and C.I. pigment brown 28; and C.I. pigment black 1 and C.I. pigment black 7.

In the case where the light shielding agent is used as the coloring agent, it is preferable to use a black pigment as the light shielding agent. Examples of the black pigment include various types of pigments irrespective of whether it is an organic substance or an inorganic substance, such as carbon black, titanium black, and a metal oxide, a composite oxide, a metal sulfide, a metal sulfate, and a metal carbonate of copper, iron, manganese, cobalt, chromium, nickel, zinc, calcium, silver, or the like. Among these, it is preferable to use the carbon black, which has a high light shielding property.

As the carbon black, known carbon black such as channel black, furnace black, thermal black, and lamp black are usable, and it is preferable to use the channel black, which is excellent in light shielding property. Also, a resin-coated carbon black may be used.

Since the resin coated carbon black has lower conductivity than the carbon black without resin coating, it is less subject to electric current leakage when used for black matrixes of liquid crystal display devices and enables producing highly reliable displays with low power consumption.

Each of the above organic pigments may be added as an auxiliary pigment as required in order to adjust a color tone of the carbon black.

Further, a dispersant may be used for uniformly dispersing the coloring agent in the negative-type photosensitive resin composition. As the dispersant, polyethylene imine-based, urethane resin-based, acryl resin-based polymer dispersants is preferably used. Particularly, in the case where the carbon black is used as the coloring agent, it is preferable to use the acryl resin-based dispersant as the dispersant.

Also, the inorganic pigments and the organic pigments may be used alone or in combination, and, in the case of combined use, the organic pigment may be used within the range of 10 to 80 parts by mass, more preferably within the range of 20 to 40 parts by mass, relative to 100 parts by mass in total of the inorganic pigment and the organic pigment.

A content of the coloring agent may appropriately be determined depending on the usage of the negative-type photosensitive resin composition, and, as one example, the content is preferably 5 to 70 parts by mass, more preferably 25 to 60 parts by mass, relative to 100 parts by mass of the solid content of the negative-type photosensitive resin composition.

Particularly, in the case of forming a black matrix by using the negative-type photosensitive resin composition, it is preferable to adjust the amount of the light shielding agent in the negative-type photosensitive resin composition so that an OD value per 1 µm of film thickness of the black matrix is 4 or more. With the OD value of 4 or more per 1 µm of film thickness in the black matrix, it is possible to attain satisfactory display contrast when the negative-type photosensitive resin composition is used for black matrixes of liquid crystal displays.

It is preferable to add to the negative-type photosensitive resin composition the coloring agent as a dispersion which is obtained by dispersing the coloring agent at an appropriate concentration by using the dispersant.

Examples of the organic solvent in the negative-type photosensitive resin composition include (poly)alkylene glycol monoalkyl ethers such as ethylene glycol monomethyl ether, ethylene glycol monoethyl ether, ethylene glycol-n-propyl ether, ethylene glycol mono-n-butyl ether, diethylene glycol monomethyl ether, diethylene glycol monoethyl ether, diethylene glycol mono-n-propyl ether, diethylene glycol mono-n-butyl ether, triethylene glycol monomethyl ether, triethylene glycol monoethyl ether, propylene glycol monomethyl ether, propylene glycol monoethyl ether, propylene glycol mono-n-propyl ether, propylene glycol mono-n-butyl ether, dipropylene glycol monomethyl ether, dipropylene glycol monoethyl ether, dipropylene glycol mono-n-propyl ether, dipropylene glycol mono-n-butyl ether, tripropylene glycol monomethyl ether, and tripropylene glycol monoethyl ether; (poly)alkylene glycol monoalkyl ether acetates such as ethylene glycol monomethyl ether acetate, ethylene glycol monoethyl ether acetate, diethylene glycol monomethyl ether acetate, diethylene glycol monoethyl ether acetate, propylene glycol monomethyl ether acetate, and propylene glycol monoethyl ether acetate; other ethers such as diethylene glycol dimethyl ether, diethylene glycol methylethyl ether, diethylene glycol diethyl ether, and tetrahydrofuran; ketones such as methyl ethyl ketone, cyclohexanone, 2-heptanone, and 3-heptanone; alkyl lactates such as methyl 2-hydroxypropionate and ethyl 2-hydroxypropionate; other esters such as ethyl 2-hydroxy-2-methylpropionate, methyl 3-methoxypropionate, ethyl 3-methoxy propionate, methyl 3-ethoxypropionate, ethyl 3-ethoxypropionate, ethyl ethoxyacetate, ethyl hydroxyacetate, methyl 2-hydroxy-3-methylbutanoate, 3-methyl-3-methoxybutylacetate, 3-methyl-3-methoxybutylpropionate, ethyl acetate, n-propyl acetate, isopropyl acetate, n-butyl acetate, isobutyl acetate, n-pentyl formate, isopentyl acetate, n-butyl propionate, ethyl butyrate, n-propyl butyrate, isopropyl butyrate, n-butyl butyrate, methyl pyruvate, ethyl pyruvate, n-propyl pyruvate, methyl acetoacetate, ethyl acetoacetate, and ethyl 2-oxobutanoate; aromatic hydrocarbons such as toluene and xylene; amides such as N-methylpyrrolidone, N,N-dimethylformamide, and N,N-dimethylacetamide; and the like. The organic solvents may be used alone or in combination of two or more kinds thereof.

Among the above organic solvents, propylene glycol monomethyl ether, ethylene glycol monomethyl ether acetate, propylene glycol monomethyl ether acetate, propyleneglycol monoethyl ether acetate, diethylene glycol dimethyl ether, diethylene glycol methylethyl ether, cyclohexanone, 3-methoxybutyl acetate are preferred since they exhibit excellent solubility with respect to the alkali-soluble resin, the photopolymerizable monomer, the photopolymerization initiator, the compound represented by the formula (1), the compound represented by the formula (10), and the compound represented by the formula (19) and improve a dispersing property of the coloring agent, and it is particularly preferable to use propylene glycol monomethyl ether acetate or 3-methoxybutyl acetate.

A content of the organic solvent is preferably such that a solid content concentration of the negative-type photosensitive resin composition is 1 to 50 mass %, more preferably 5 to 30 mass %.

The negative-type photosensitive resin composition may contain various additives as required. Examples of the additives include a sensitizer, a curing accelerator, a filler, an adhesion accelerator, an antioxidant, an ultraviolet ray absorber, a flocculation inhibitor, thermal polymerization inhibitor, an anti-foaming agent, a surfactant, and the like.

The negative-type photosensitive resin composition is prepared by mixing each of the above-described components with a stirring machine. In order that the prepared negative-type photosensitive resin composition becomes homogenous, the negative-type photosensitive resin composition may be filtered using a membrane filter or the like.

The present invention has been described above. Novel fluorene-based compounds according to the present invention have a high reactivity with respect to conventional fluorene-based compounds while maintaining excellent optical properties and thermal properties. That is, in resin and materials for resins, in order to impart or improve, for example, thermal properties such as heat resistance and optical properties such as high refractive index, for example, the selection of monomer components or the addition of compounds that can modify resins have hitherto been made. Under these circumstances, compounds having a fluorene skeleton (for example, a 9,9-bisphenylfluorene skeleton) have been used. However, conventional fluorene compounds, for example, fluorene-based acrylates had a low reactivity. The present invention can provide novel fluorene-based compounds having a high reactivity while maintaining excellent optical properties and thermal properties, polymerizable monomers including the fluorene-based compounds, and crosslinking agents including the fluorene-based compounds.

EXAMPLES

Hereinafter, the present invention will be described more specifically with examples, but the scope of the present invention is not limited to these examples.

Compounds Represented by the Formula (1) and Comparative Compounds

Compounds 1 to 3 represented by the following formulae were provided as the compounds represented by the general formula (1). Further, for comparison, Comparative Compounds 1 to 6 represented by the following formulae were provided.

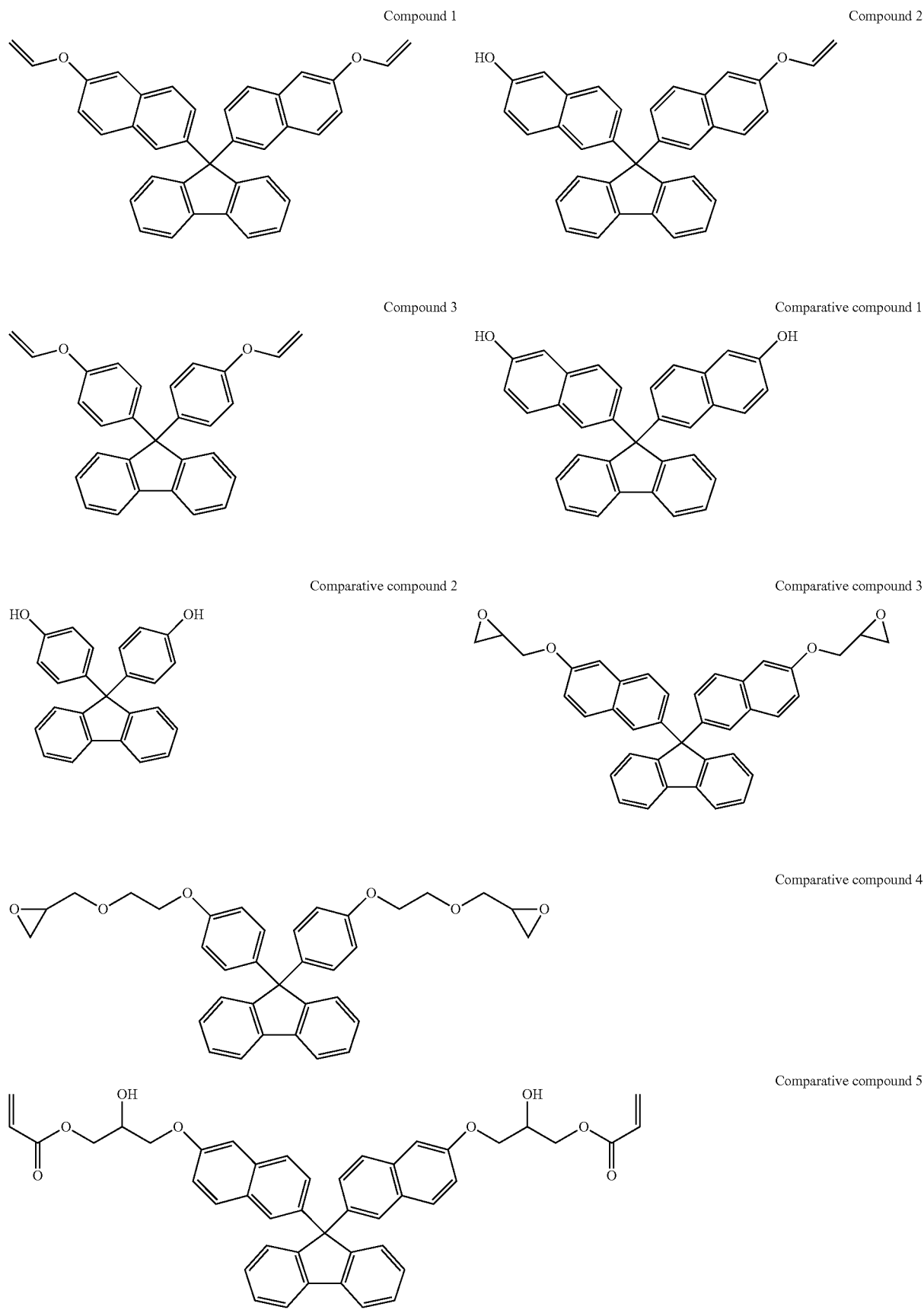

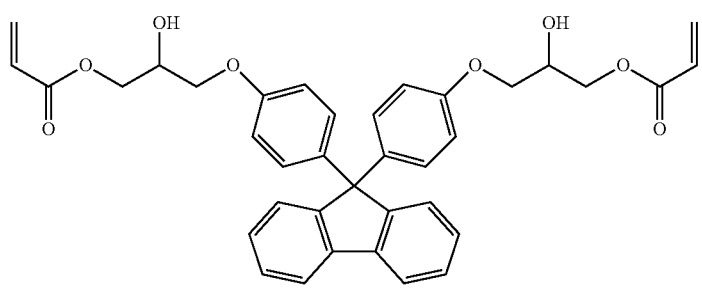

Comparative compound 6

Synthesis methods for Compounds 1 to 3 will be described below (Synthesis Examples 1 to 3). Materials used in Synthesis Examples were as follows.
[Inorganic Base]
(1) Light Ash Sodium Carbonate
  Particle diameter distribution: 250 μm or more; 3% by weight
    150 μm (inclusive) to 250 μm (exclusive); 15% by weight
    75 μm (inclusive) to 150 μm (exclusive); 50% by weight
    Less than 75 μm; 32% by weight
  The particle diameter distribution was determined by sieving particles with sieves of 60 meshes (250 μm), 100 meshes (150 μm), and 200 meshes (75 μm) and measuring the weight of oversize particles and undersize particles.
[Transition Element Compound Catalyst]
(1) di-μ-chlorobis(1,5-cyclooctadiene)diiridium(I): [Ir(cod)Cl]$_2$
[Hydroxy Compound]
(1) 9,9'-Bis(6-hydroxy-2-naphthyl)fluorene
(2) 9,9'-Bis(4-hydroxyphenyl)fluorene
[Vinyl Ester Compound]
  (1) Vinyl propionate

[Synthesis Example 1] Synthesis of Compound 1

A 1000-ml reaction vessel equipped with a cooling pipe and a decanter that conducts separation of a condensate and returns an organic layer to the reaction vessel and discharges a water layer to the outside of the system was charged with di-μ-chlorobis(1,5-cyclooctadiene)diiridium(I) [Ir(cod)Cl]$_2$ (839 mg, 1.25 mmol), light ash sodium carbonate (12.7 g, 0.12 mol), 9,9'-bis(6-hydroxy-2-naphthyl)fluorene (225 g, 0.5 mol), vinyl propionate (125 g, 1.25 mol), and toluene (300 ml). Thereafter, the temperature of the system was gradually raised while stirring with a stirring blade having a surface area of 10 cm$^2$ at a rotation speed of 250 rpm, followed by reflux. A reaction was allowed to proceed for 5 hr under reflux while removing water produced as by-product with the decanter. The reaction solution was analyzed by gas chromatography. As a result, it was found that the conversion of 9,9'-bis(6-hydroxy-2-naphthyl)fluorene was 100%, and 9,9'-bis(6-vinyloxy-2-naphthyl)fluorene (Compound 1) and bis-6-naphthofluorene monovinyl ether were produced at yields of 81% and 4%, respectively, based on 9,9'-bis(6-hydroxy-2-naphthyl)fluorene.
$^1$H-NMR (CDCl$_3$): 4.47 (dd, 2H, J=1.5 Hz, 5.0 Hz), 4.81 (dd, 2H, J=3.5 Hz, 12.0 Hz), 6.71 (dd, 2H, J=6.0 Hz), 7.12-7.82 (m, 20H)

[Synthesis Example 2] Synthesis of Compound 2 (Isolation)

The reaction product obtained in Synthesis Example 1 was subjected to separation and purification by column chromatography on silica gel to isolate bis-6-naphthofluorene monovinyl ether (Compound 2).
$^1$H-NMR (CDCl$_3$): 4.55 (dd, 1H, J=6.0 Hz), 4.88 (dd, 1H, J=3.5 Hz), 6.79 (dd, 1H, J=6.0 Hz, 14.0 Hz), 7.20-7.89 (m, 20H)

[Synthesis Example 3] Synthesis of Compound 3

A 1000-ml reaction vessel equipped with a cooling pipe and a decanter that conducts separation of a condensate and returns an organic layer to the reaction vessel and discharges a water layer to the outside of the system was charged with di-μ-chlorobis(1,5-cyclooctadiene)diiridium(I) [Ir(cod)Cl]$_2$ (839 mg, 1.25 mmol), light ash sodium carbonate (12.7 g, 0.12 mol), 9,9'-bis(4-hydroxyphenyl)fluorene (186 g, 0.5 mol), vinyl propionate (125 g, 1.25 mol), and toluene (300 ml). Thereafter, the temperature of the system was gradually raised while stirring with a stirring blade having a surface area of 10 cm$^2$ at a rotation speed of 250 rpm, followed by reflux. A reaction was allowed to proceed for 5 hr under reflux while removing water produced as by-product with the decanter. The reaction solution was analyzed by gas chromatography. As a result, it was found that the conversion of 9,9'-bis(4-hydroxyphenyl)fluorene was 100%, and 9,9'-bis(4-vinyloxyphenyl)fluorene (Compound 3) and bis-4-phenolfluorene monovinyl ether were produced at yields of 72% and 9%, respectively, based on 9,9'-bis(4-hydroxyphenyl)fluorene.
$^1$H-NMR (CDCl$_3$): 4.47 (dd, 2H), 4.81 (dd, 2H), 6.71 (dd, 2H), 7.12-7.82 (m, 16H)
Evaluation Compounds 1 and 3 and Comparative Compounds 1 to 6 were dissolved in propylene glycol monomethyl ether acetate to prepare solutions having a concentration of 20% by mass. The solutions were coated with a spin coater on a glass substrate, and the coatings were prebaked at 100° C. for 120 sec to form dried coatings (coating thickness 2.0 μm). The dried coatings were postbaked at 230° C. for 20 min to obtain cured films (film thickness 1.7 μm).

In order to evaluate the reactivity of Compounds 1 and 3 and Comparative Compounds 1 to 6, for the cured films, the pencil hardness was measured according to JIS K 5400. The higher the pencil hardness, the higher the reactivity of the compound.

For the cured films (for the dried coatings when the cured film was not obtained), a light transmittance at a wavelength of 633 nm and a refractive index were measured as optical parameters.

Further, in order to evaluate the heat resistance of the cured films, the cured films were heated from room temperature (about 20° C.) at a temperature rise rate of 10° C. per min to conduct a thermogravimetric analysis in the air.

In the thermogravimetric analysis, a temperature at which the mass was reduced by 5% based on the mass of the cured films at the start of the analysis, $T_{d5\%}$, was measured.

The results of measurement are shown in Table 1.

TABLE 1

|  | Pencil hardness | Light transmittance | Refractive index | $T_{d5\%}$ (° C.) |
|---|---|---|---|---|
| Compound 1 | 7 H | 98% | 1.74 | 357 |
| Compound 3 | 6 H | 98% | 1.65 | 335 |
| Comparative compound 1 | Uncured | 90% | 1.72 | — |
| Comparative compound 2 | Uncured | 94% | 1.63 | — |
| Comparative compound 3 | 5 H | 97% | 1.69 | 400 |
| Comparative compound 4 | 4 H | 97% | 1.59 | 376 |
| Comparative compound 5 | 2 H | 88% | 1.67 | 396 |
| Comparative compound 6 | 3 H | 92% | 1.57 | 389 |

As is apparent from Table 1, the cured films obtained from Compounds 1 and 3 had a high pencil hardness, and these compounds had a high reactivity. For the cured films obtained from Compounds 1 and 3, the light transmittance met a value of not less than 98% that is required of recent functional membranes, and the refractive index and the heat resistance were good.

On the other hand, the cured films obtained from Comparative Compounds 1 to 6 had a lower pencil hardness than the cured films obtained form Compounds 1 and 3, and Comparative Compounds 1 to 6 had an inferior reactivity. Further, the cured films obtained from Comparative Compounds 1 to 6 were inferior in light transmittance to the cured films obtained from Compounds 1 and 3.

Synthesis Examples Through Leaving Group-Containing Fluorene-Based Compounds

Synthesis Example 4

6,6'-(9-Fluorenylidene)-bis(2-naphthyloxyethanol) (598 g, 1.11 mol), pyridine (87.8 g, 1.11 mol), and dipropylene glycol dimethyl ether (1670 mL) were added to a 5-L reactor, the atmosphere of the system was replaced by nitrogen, and the temperature was raised to 60° C. Thionyl chloride (395.9 g, 3.33 mol) was added dropwise over a time period of 3 hr, followed by ripening for 2 hr. The reaction solution was cooled to 30° C., water was added to stop the reaction, and methanol was added dropwise at a temperature in the range of 15 to 20° C. to obtain a target compound with the hydroxyl group replaced by chlorine at a yield of 96% (compound represented by the following formula; the compound being referred to also as Compound 4).

$^1$H-NMR (CDCl$_3$): 3.85 (t, 4H, J=6.0 Hz), 4.31 (t, 4H, J=6.0 Hz), 7.08-7.82 (m, 20H)

Compound 4

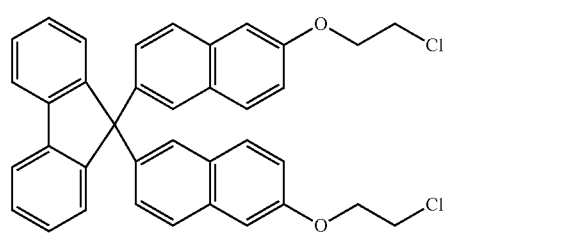

Synthesis Example 5

A solution of potassium-t-butoxide (327.5 g, 2.92 mol) in tetrahydrofuran (1260 mL) was added dropwise at a temperature in the range of 20° C. to 40° C. to a 5-L reactor that had been charged with Compound 4 (560 g, 0.97 mol) and tetrahydrofuran (1260 mL). The reaction solution was ripened at 60° C. for 2 hr. Water was added to stop the reaction. The organic layer was separated and concentrated in an evaporator to a weight that was twice larger than the charged amount of Compound 4. The concentrate was added dropwise to methanol to obtain 9,9'-bis(6-vinyloxy-2-naphthyl) fluorene (compound represented by the following formula, that is, Compound 1) as a white or grayish white solid at a yield of 77%.

$^1$H-NMR (CDCl$_3$): 4.48 (dd, 2H, J=1.5 Hz, 6.5 Hz), 4.81 (dd, 2H, J=1.5 Hz, 13.5 Hz), 6.73 (dd, 2H, J=6.5 Hz, 13.5 Hz), 7.13-7.83 (m, 20H)

Compound 1

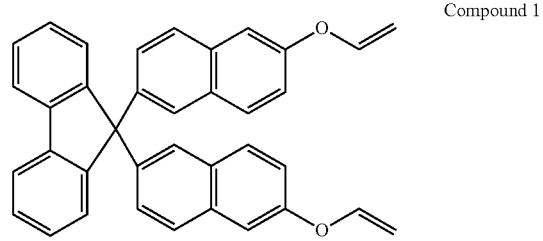 [SMILES: C=COc1ccc2cc(C3(c4ccc5cc(OC=C)ccc5c4)c4ccccc4-c4ccccc43)ccc2c1]

Synthesis Example 6

Ethylene glycol (1.00 g, 0.0161 mol), triethylamine (3.42 g, 0.0338 mol), and tetrahydrofuran (3.38 mL) were added to a 25-mL reactor. The atmosphere of the reactor was replaced by nitrogen, and the system was cooled to 0° C. Methanesulfonyl chloride (3.88 g, 0.0338 mol) was added dropwise over a time period of 2 hr. The reaction solution was ripened for one hr, and water was added to stop the reaction. Ethyl acetate was added, the organic layer was separated, and the solvent was removed by evaporation in an evaporator to obtain a compound that was ethylene glycol at a yield of 80% with a methanesulfonyl group added thereto (compound represented by the following formula; hereinafter referred to also as "EG-DMs")

$^1$H-NMR (CDCl$_3$): 3.10 (s, 6H), 4.47 (s, 4H)

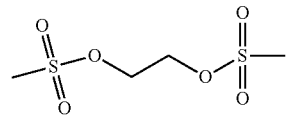

EG-DMs

Synthesis Example 7

6,6-(9-Fluorenylidene)-2,2-dinaphthol (compound represented by the following formula indicated on the left side; 1.00 g, 0.0022 mol; hereinafter referred to also as "Compound 5"), potassium carbonate (0.64 g, 0.0047 mol), and tetrahydrofuran (3.38 mL) were added to a 25-mL reactor. The atmosphere of the reactor was replaced by nitrogen. A solution of EG-DMs (1.02 g, 0.0047 mol) synthesized in Synthesis Example 6 in tetrahydrofuran (1.12 mL) was added at room temperature, the mixture was heated to 60° C., and the reaction solution was ripened for 15 hr. The reaction solution was analyzed by HPLC. As a result, it was found that Compound 6 (compound represented by the following formula indicated on the right side) was synthesized at a conversion of Compound 5 of 99% and a selectivity of 65%.

(Compound 6) $^1$H-NMR (CDCl$_3$): 3.08 (s, 6H), 4.32 (t, 4H, J=4.4 Hz), 4.60 (t, 4H, J=4.4 Hz), 7.05-7.83 (m, 20H)

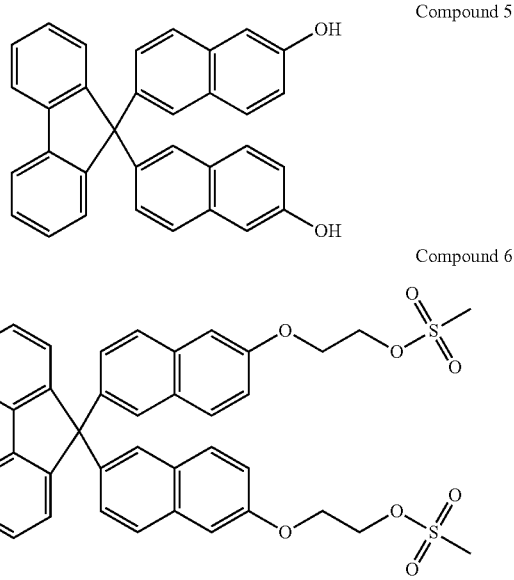

Compound 5

Compound 6

Synthesis Example 8

A solution of potassium-t-butoxide (1.45 g, 0.0130 mol) in tetrahydrofuran (2.25 mL) was added dropwise at a temperature in the range of 20° C. to 40° C. to a 25-mL reactor charged with Compound 6 (2.00 g, 0.00288 mol), dipropylene glycol dimethyl ether (2.25 mL). The reaction solution was ripened at 100° C. for 2 hr. The reaction solution was analyzed by HPLC. As a result, it was found that Compound 1 was synthesized at a conversion of Compound 6 of 99% and a selectivity of 58% and a monovinyl monomesyl compound (compound represented by the following formula; hereinafter referred to also as "Compound 7") was synthesized at a selectivity of 32%.

$^1$H-NMR (CDCl$_3$): 3.10 (s, 3H), 4.34 (t, 2H, J=3.6 Hz), 4.49 (dd, 1H, J=1.2 Hz, 5.2 Hz), 4.62 (t, 2H, J=3.6 Hz), 4.81 (dd, 1H, J=1.2 Hz, 11.2 Hz), 6.73 (dd, 1H, J=5.2 Hz, 11.2 Hz), 7.06-7.83 (m, 20H)

Compound 7

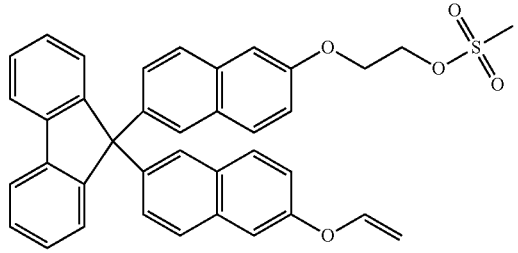

Synthesis Example 9

2-Chloroethanol (3.00 g, 0.048 mol), triethylamine (5.87 g, 0.058 mol), and tetrahydrofuran (10.12 mL) were added to a 50-mL reactor. The atmosphere in the reactor was replaced by nitrogen. Thereafter, the reaction solution was cooled to 0° C. Methanesulfonyl chloride (6.09 g, 0.053 mol) was added dropwise over a time period of 2 hr. The reaction solution was ripened for one hr. Water was added to stop the reaction. Ethyl acetate was added, the organic layer was separated, and the solvent was removed by evaporation in an evaporator to obtain a compound that was 2-chloroethanol with a methanesulfonyl group added thereto (compound represented by the following formula; hereinafter referred to also as "ClEMs") at a yield of 80%.

$^1$H-NMR (CDCl$_3$): 3.09 (s, 3H), 3.77 (t, 2H, J=5.5 Hz), 4.45 (t, 2H, J=5.5 Hz)

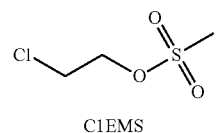

ClEMS

Synthesis Example 10

Compound 5 (1.00 g, 0.0022 mol), potassium carbonate (0.64 g, 0.0047 mol), and dipropylene glycol dimethyl ether (2.23 mL) were added to a 25-mL reactor. The atmosphere in the reactor was replaced by nitrogen. A solution of ClEMs (1.06 g, 0.0067 mol) in dipropylene glycol dimethyl ether (1.12 mL) was added at room temperature. The mixture was heated to 60° C., and the reaction mixture was ripened for 15 hr. The reaction solution was analyzed by HPLC. As a result, it was found that Compound 4 was synthesized at a conversion of Compound 5 of 17% and a selectivity of 4% and Compound 8 (compound represented by the following formula) was synthesized at a selectivity of 12%.

$^1$H-NMR (CDCl$_3$): 3.86 (t, 2H, J=6.0 Hz), 4.32 (t, 2H, J=6.0 Hz), 7.09-7.82 (m, 20H)

Compound 8

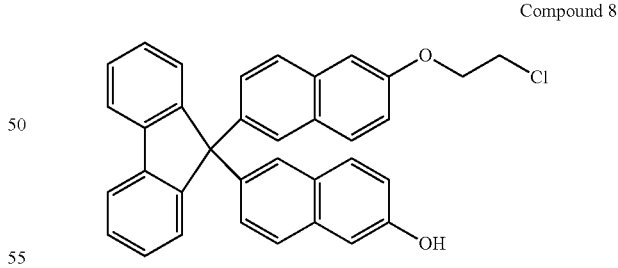

Synthesis Example 11

A solution of potassium-t-butoxide (0.58 g, 0.0052 mol) in tetrahydrofuran (6.8 mL) was added dropwise at a temperature in the range of 20° C. to 40° C. to a 25-mL reactor charged with Compound 4 (3.0 g, 0.0052 mol) and tetrahydrofuran (6.8 mL). The reaction solution was ripened at 60° C. for 2 hr. Water was then added to stop the reaction. The organic layer was analyzed by HPLC. As a result, it was found that Compound 1 was synthesized at a conversion of Compound 4 of 57% and a selectivity of 25% and a monovinyl monochloro compound (compound represented by the following formula; hereinafter referred to also as "Compound 9") was synthesized at a selectivity of 75%.

$^1$H-NMR (CDCl$_3$): 3.84 (t, 2H, J=6.0 Hz), 4.30 (t, 2H, J=6.0 Hz), 4.48 (dd, 1H, J=1.6 Hz, 6.0 Hz), 4.81 (dd, 1H, J=1.6 Hz, 13.6 Hz), 6.72 (dd, 1H, J=6.0 Hz, 13.6 Hz), 7.08-7.82 (m, 20H)

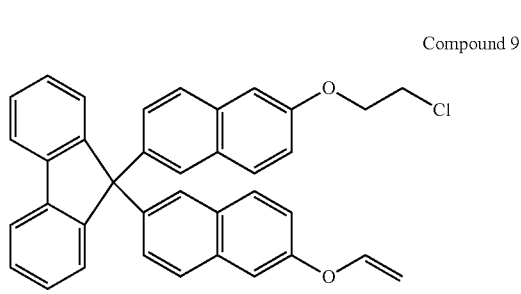 [SMILES: C=COc1ccc2cc(C3(c4ccc5cc(OCCCl)ccc5c4)c4ccccc4-c4ccccc43)ccc2c1]

Compound 9

Synthesis Example 12

9,9'-Bis(4-(2-hydroxyethoxy)phenyl)fluorene (6.26 g, 0.0143 mol), pyridine (2.82 g, 0.0357 mol), dipropylene glycol dimethyl ether (33.4 mL), and tetrahydrofuran (33.7 mL) were added to a 200-mL reactor. The atmosphere in the reactor was replaced by nitrogen. The reaction solution was heated to 60° C. Thionyl chloride (6.79 g, 0.0571 mol) was added dropwise over a time period of 2 hr. The reaction solution was then ripened for 2 hr. After cooling to 30° C., water was added to stop the reaction, and methanol was added dropwise at a temperature in the range of 15 to 20° C. to obtain a target compound in which the hydroxyl group was replaced with chlorine (compound represented by the following formula; hereinafter referred to also as "Compound 10") at a yield of 95%.

$^1$H-NMR (CDCl$_3$): 3.75 (t, 4H, J=6.0 Hz), 4.14 (t, 4H, J=6.0 Hz), 6.73-7.75 (m, 16H)

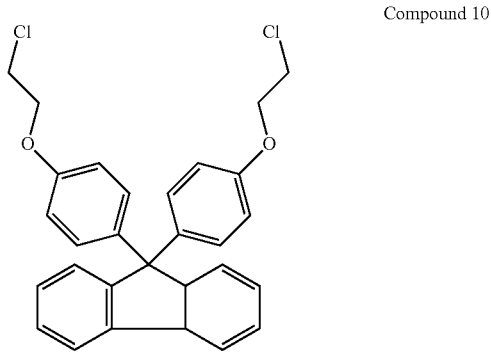 [SMILES: ClCCOc1ccc(C2(c3ccc(OCCCl)cc3)c3ccccc3C3C=CC=CC32)cc1]

Compound 10

Synthesis Example 13

A solution of potassium-t-butoxide (3.53 g, 0.0315 mol) in tetrahydrofuran (13.6 mL) was added dropwise at a temperature in the range of 20° C. to 40° C. to a 100-mL reactor charged with Compound 10 (5.0 g, 0.0105 mol) and tetrahydrofuran (11.5 mL). The reaction solution was ripened at 60° C. for 2 hr. Water was then added to stop the reaction. The organic layer was separated and concentrated in an evaporator to a weight that was twice larger than the charged amount of Compound 10. The concentrate was added dropwise to methanol to obtain 9,9'-bis(4-vinyloxyphenyl)fluorene (compound represented by the following formula, that is, Compound 3), as a white or grayish white solid at a yield of 79%.

$^1$H-NMR (CDCl$_3$): 4.47 (dd, 2H), 4.81 (dd, 2H), 6.71 (dd, 2H), 7.12-7.82 (m, 16H)

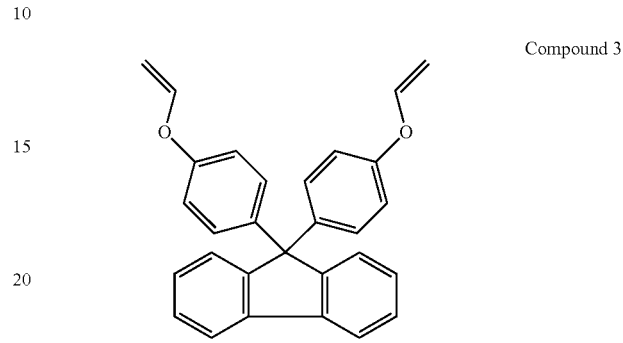

Compound 3

Compounds Represented by General Formula (19)

Synthesis Example 14

Compound 5 (3.00 g, 0.00666 mol), triethylamine (1.48 g, 0.0146 mol), phenothiazine (9.00 mg, 0.0000452 mol), and tetrahydrofuran (16.9 mL) were added to a 50-mL reactor. The atmosphere in the reactor was replaced by nitrogen. The reaction solution was cooled to 0° C. Acryloyl chloride (1.51 g, 0.0166 mol) was added dropwise over a time period of one hr, and the reaction solution was ripened for 2 hr. Water was added to stop the reaction, and the organic layer was separated. The solvent was removed by evaporation in an evaporator, and the residue was then purified by column chromatography on silica gel to obtain a target diacryl compound (compound represented by the following formula; hereinafter referred to also as "Compound 11") as a white solid at a yield of 63%.

$^1$H-NMR (CDCl$_3$): 6.03 (dd, 2H, J=1.5 Hz, 10.0 Hz), 6.36 (dd, 2H, J=10.0 Hz, 17.5 Hz), 6.63 (dd, 2H, J=1.5 Hz, 17.5 Hz), 7.19-7.84 (m, 20H)

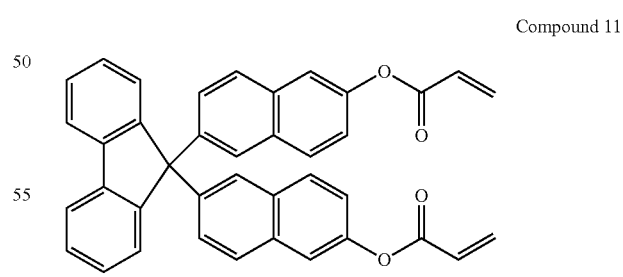

Compound 11

Synthesis Example 15

Compound 5 (3.00 g, 0.00666 mol), triethylamine (1.48 g, 0.0146 mol), phenothiazine (9.00 mg, 0.0000452 mol), and tetrahydrofuran (16.9 mL) were added to a 50-mL reactor. The atmosphere in the reactor was replaced by nitrogen. The reaction solution was then cooled to 0° C. Methacryloyl chloride (1.74 g, 0.0166 mol) was added dropwise over a time period of one hr, and the reaction solution was then gradually heated to 40° C. and ripened for 2 hr. Water was added to stop the reaction, and the organic layer was separated. The solvent was removed by evaporation in an evaporator, and the residue was purified by column chromatography on silica gel to obtain a target dimethacryl compound (compound represented by the following formula; hereinafter referred to also as "Compound 12") as a white solid at a yield of 73%.

$^1$H-NMR (CDCl$_3$): 2.08 (s, 6H), 5.77 (s, 2H), 6.38 (s, 2H), 7.18-7.84 (m, 20H)

Compound 12

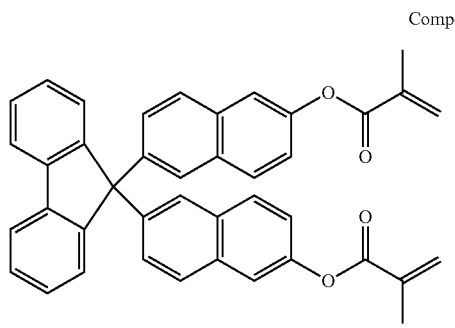

Carbon dispersion "CF black" (tradename: manufactured by Mikoku Color Ltd., solid content 25%, solvent: 3-methoxybutyl acetate) . . . 400 parts by mass The resin (R-1) was synthesized by the following method.

At the outset, a 500-mL four-necked flask was charged with 235 g of a bisphenolfluorene epoxy resin (epoxy equivalent 235), 110 mg of tetramethyl ammonium chloride, 100 mg of 2,6-di-tert-butyl-4-methylphenol, and 72.0 g of acrylic acid. The contents were heat-dissolved at 90 to 100° C. while blowing air thereinto at a rate of 25 ml/min. Next, in such a state that the solution was cloudy, the solution was gradually heated to 120° C. for full dissolution. In this case, the solution gradually became transparent and viscous but was continued to be stirred. In this period, the acid value was measured, and heating with stirring was continued until the acid value reached less than 1.0 mg KOH/g. A time period of 12 hr was necessary until the acid value reached a target value. The solution was then cooled to room temperature to obtain a bisphenolfluorene epoxy acrylate that was colorless, transparent and solid and represented by the following formula (r-4)

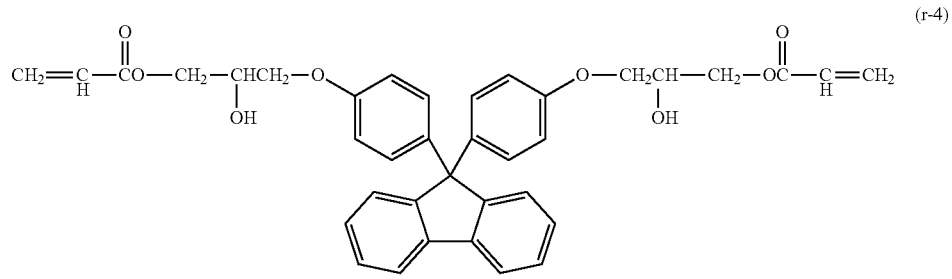

(r-4)

Preparation of Negative-Type Photosensitive Resin Composition

Example 1

The following ingredients were added to a mixed solvent of 3-methoxybutyl acetate (MA)/tetramethylurea (TMU)/propylene glycol monomethyl ether acetate (PM)=55/10/35 (mass ratio). The mixture was mixed with a stirrer for one hr and filtered through a 5-µm membrane filter to prepare a negative-type photosensitive resin composition having a solid content of 15% by mass as a filtrate.
  An alkali-soluble resin
  Resin (R-1) (solid content 55%, solvent: 3-methoxybutyl acetate) . . . 60 parts by mass
  Photopolymerizable monomer
  Dipentaerythritol hexaacrylate (DPHA, manufactured by Nippon Kayaku Co., Ltd.) . . . 20 parts by mass
  Photopolymerization initiator
  "OXE-02" (tradename: manufactured by BASF) . . . 10 parts by mass
  Compound represented by general formula (1)
  Compound 1 . . . 10 parts by mass
  Coloring Agent Next, 600 g of 3-methoxybutyl acetate was added to and dissolved in 307.0 g of the bisphenolfluorene epoxy acrylate. 80.5 g of benzophenone tetracarboxylic acid dianhydride and 1 g of tetraethylammonium bromide were mixed into the solution. The mixture was gradually heated, and a reaction was allowed to proceed at 110 to 115° C. for 4 hr. After the disappearance of an acid anhydride group, 38.0 g of 1,2,3,6-tetrahydro phthalic anhydride was mixed thereinto, and a reaction was allowed to proceed at 90° C. for 6 hr to obtain a resin (R-1). The disappearance of the acid anhydride group was confirmed by an IR spectrum.

The resin (R-1) corresponds to a compound represented by the general formula (r-1).

Example 2 and Comparative Examples 1 to 6

In Example 2 and Comparative Examples 2 to 6, negative-type photosensitive resin compositions were prepared in the same manner as in Example 1, except that Compound 3 and Comparative Compound 1 to 5 were used instead of Compound 1. Further, in Comparative Example 1, a negative-type photosensitive resin composition was prepared in the same manner as in Example 1, except that Compound 1 was not used.

[Evaluation]

Negative-type photosensitive resin compositions of Examples 1 and 2 and Comparative Examples 1 to 6 were spin-coated on a glass substrate (100 mm×100 mm), and the coatings were prebaked at 90° C. for 120 sec to form coatings having a thickness of 1.0 μm. Next, the coatings were irradiated with ultraviolet light using a mirror projection aligner (product name: TME-150RTO, manufactured by Topcon Corp.) at an exposure gap of 50 μm through a negative mask with a line pattern of 5, 10, 15, and 20 μm formed therein. The exposure was 10 mJ/cm². After exposure, the coating films were developed with a 0.04 mass % aqueous KOH solution of 26° C. for 40 sec and postbaked at 230° C. for 30 min to form line patterns.

The line patterns thus formed were observed under an optical microscope to evaluate pattern adhesion. The pattern adhesion was evaluated as "good" when the line pattern was formed without separation from the substrate; and was evaluated as "no adhesion" when the line pattern was not formed due to separation from the substrate.

The results are shown in Table 3 below.

TABLE 2

| | Compound of formula (1) or comparative compound | Adhesion of pattern | | | |
|---|---|---|---|---|---|
| | | 5 μm | 10 μm | 15 μm | 20 μm |
| Example 1 | Compound 1 | Good | Good | Good | Good |
| Example 2 | Compound 3 | Good | Good | Good | Good |
| Comparative Example 1 | None | None | None | Good | None |
| Comparative Example 2 | Comparative Example 1 | None | None | Good | None |
| Comparative Example 3 | Comparative Example 2 | None | Good | None | None |
| Comparative Example 4 | Comparative Example 3 | None | Good | None | None |
| Comparative Example 5 | Comparative Example 4 | None | None | Good | None |
| Comparative Example 6 | Comparative Example 5 | None | None | Good | None |

As is apparent from Table 3, when the negative-type photosensitive resin compositions of Examples 1 and 2 containing Compounds 1 and 3 represented by the general formula (1) were used, a 5-μm line pattern was closely adhered to substrate even at a low exposure of 10 mJ/cm².

On the other hand, when the negative-type photosensitive resin composition of Comparative Example 1 free from the compound represented by the general formula (1), and the negative-type photosensitive resin compositions of Comparative Examples 2 to 6 that were free from the compound represented by the general formula (1) and contained Comparative Compounds 1 to 5 were used, as is apparent from Table 3, the pattern adhesion was inferior to that in Examples 1 and 2 and good micropatterning properties could not be obtained.

The invention claimed is:

1. A vinyl-group-containing fluorene-based compound represented by the following formula (1):

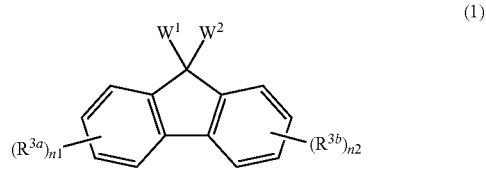

wherein $W^1$ and $W^2$ each independently represent a group represented by the following formula (2), a group represented by the following formula (4), a hydroxyl group, or a (meth)acryloyloxy group, provided that $W^1$ and $W^2$ do not simultaneously represent a hydroxyl group or the group represented by the following formula (4), and at least one of $W^1$ and $W^2$ represents a group represented by the formula (2); $R^{3a}$ and $R^{3b}$ each independently represent a cyano group, a halogen atom, or a monovalent hydrocarbon group; and n1 and n2 each independently represent an integer of 0 to 4,

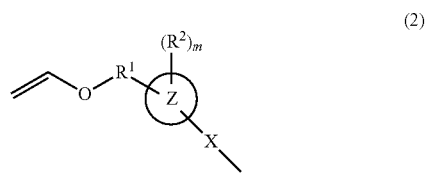

wherein a ring Z represents a fused aromatic hydrocarbon ring; X represents a single bond or —S—; $R^1$ represents a single bond; $R^2$ represents substituent group A or B, wherein substituent group A represents a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, or a sulfo group; and substituent group B represents a group formed by substituting at least a part of hydrogen atoms bonded to carbon atoms of the substituents contained in substituent group C below with a monovalent hydrocarbon group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group, wherein substituent group C represents a monovalent hydrocarbon group, a group represented by —$OR^{4a}$, a group represented by —$SR^{4b}$, an acyl group, an alkoxycarbonyl group, a group represented by —$NHR^{4c}$ or a group represented by —$N(R^{4d})_2$;

$R^{4a}$ to $R^{4d}$ each independently represent a monovalent hydrocarbon group; and m is an integer of 0 or more, and

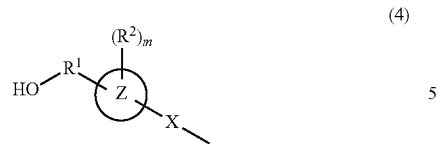 (4)
wherein a ring Z, X, $R^1$, $R^2$, and m are as defined above.
2. The vinyl-group-containing fluorene-based compound according to claim 1, wherein the ring Z is a naphthalene ring.
* * * * *